United States Patent
Irudayaraj et al.

(10) Patent No.: US 11,761,958 B2
(45) Date of Patent: Sep. 19, 2023

(54) DEVICES, SYSTEMS, AND METHODS FOR THE DETECTION OF A TARGET ANALYTE USING MAGNETIC FOCUS LATERAL FLOW IMMUNOASSAY TECHNIQUES

(71) Applicant: Purdue Research Foundation, West Lafayette, IN (US)

(72) Inventors: Joseph M K Irudayaraj, West Lafayette, IN (US); Wen Ren, Urbana, IL (US)

(73) Assignee: Purdue Research Foundation, West Lafayette, IN (US)

(*) Notice: Subject to any disclaimer, the term of this patent is extended or adjusted under 35 U.S.C. 154(b) by 972 days.

(21) Appl. No.: 16/305,731

(22) PCT Filed: Jul. 12, 2017

(86) PCT No.: PCT/US2017/041724
§ 371 (c)(1),
(2) Date: Nov. 29, 2018

(87) PCT Pub. No.: WO2018/013697
PCT Pub. Date: Jan. 18, 2018

(65) Prior Publication Data
US 2020/0124595 A1    Apr. 23, 2020

(51) Int. Cl.
*G01N 33/543* (2006.01)
*G01N 21/78* (2006.01)
(Continued)

(52) U.S. Cl.
CPC ....... *G01N 33/54388* (2021.08); *G01N 21/78* (2013.01); *G01N 33/54326* (2013.01); *G01N 33/56911* (2013.01); *G01N 33/57411* (2013.01)

(58) Field of Classification Search
CPC ............. G01N 33/54326; G01N 21/78; G01N 33/56911; G01N 33/57411; G01N 33/558;
(Continued)

(56) References Cited

U.S. PATENT DOCUMENTS 7,285,424 B2 * 10/2007 Song ................ G01N 33/54326
                                                   436/514
7,390,675 B2 *  6/2008 Feistel ................ G01N 33/558
                                                   436/514

(Continued)

FOREIGN PATENT DOCUMENTS

WO    2015040377 A1    3/2015
WO    2017138946 A1    8/2017

OTHER PUBLICATIONS

International Searching Authority, International Search Report, PCT Patent Application Serial No. PCT/US17/41724, dated Dec. 28, 2017.

(Continued)

*Primary Examiner* — Christopher L Chin
(74) *Attorney, Agent, or Firm* — Reichel Stohry Dean LLP; Natalie J. Dean

(57) ABSTRACT

Devices, systems, and methods are provided for magnetic focus enhanced lateral flow assays. The devices and systems are ultrasensitive and provide for the visual detection of the presence or absence of one or more target analytes—which may include pathogens, proteins, or even molecules smaller than the foregoing—even when such analytes are only present in very limited amounts. The devices and systems include an immunostrip with a magnet positioned adjacent thereto, and magnetic probes specific to a target analyte that bind to the target analyte with specificity if present within a fluid sample to be tested. Methods are also provided for detecting one or more target analytes using magnetic focus, such methods including a step of controlling movement of a (Continued)

target analyte complex on an immunostrip incorporating a magnetic field, where such control slows a flow of the target analyte complex through a capture area on the immunostrip.

18 Claims, 20 Drawing Sheets

(51) Int. Cl.
G01N 33/569 (2006.01)
G01N 33/574 (2006.01)

(58) Field of Classification Search
CPC ........ G01N 33/54387; G01N 33/54389; B01L 2300/0825
USPC ....... 422/400, 401, 420, 421, 425, 426, 430; 435/7.5, 7.92, 7.94, 28, 287.7, 287.9, 970, 435/810; 436/169, 170, 514, 518, 526, 436/530, 810
See application file for complete search history.

(56) References Cited

U.S. PATENT DOCUMENTS

| | | | |
|---|---|---|---|
| 7,879,597 B2* | 2/2011 | Esfandiari | G01N 33/54386 436/514 |
| 8,603,835 B2* | 12/2013 | Esfandiari | G01N 33/54386 436/514 |
| 2002/0094548 A1* | 7/2002 | Feistel | G01N 33/54333 435/7.92 |
| 2005/0130293 A1 | 6/2005 | Blatt et al. | |
| 2007/0020700 A1* | 1/2007 | Carpenter | H01F 1/0054 435/7.5 |
| 2011/0200530 A1 | 8/2011 | Allemann et al. | |
| 2016/0011183 A1 | 1/2016 | Egan et al. | |
| 2016/0054311 A1 | 2/2016 | Marks et al. | |

OTHER PUBLICATIONS

International Searching Authority, Written Opinion of the International Searching Authority, PCT Patent Application Serial No. PCT/US17/41724, dated Dec. 28, 2017.

Ren, W. et al., Ultrasensitive detection of microbial cells using magnetic focus enhanced lateral flow sensors, Chemical Communications, Mar. 18, 2016; vol. 52: 4930-4933, GB.

Mohammed, S. et al., Point-of-care test for cervical cancer in LMICs, Oncotarget, Feb. 25, 2016; vol. 7(14): 18787-18797.

Lu, W. et al., Dual immunomagnetic nanobeads-based lateral flow test strip for simultaneous quantitative detection of carcinoembryonic antigen and neuron specific enolase, Scientific Reports, Feb. 10, 2017; vol. 7(42414): 1-10.

* cited by examiner

| Product/company | Target analysis | Principle | Signal generation | Simplicity | Quantitative | Clinical sensitivity | Analysis time |
|---|---|---|---|---|---|---|---|
| APTIMA HPV Assay/ Gen-Probe | HPR mRNA (14 types) | Multiplex nucleic acid | - | Complex | No (qualitative) | 92% | 6 hours (180 specimen) |
| NucliSENS EasyQ® HPV/ Biomerieux | HPV mRNA (5 types) | Real-time nucleic acid amplification | - | Complex | No (qualitative) | 63% | 4 hours |
| Cobas® 4800 HPV System/Roche | HPV DNA (14 types) | Real-time PCR assay | - | Relatively simple (Fully automated) | No (qualitative) | 90% | - |
| CareHPV™/Qiagen Inc. (collaboration with PATH) | HPV DNA (14 types) | DNA hybridization/ immunoassay | Chemiluminescence | Relative simple | No (qualitative) | 90% | 2.5 hours |
| Digene HC2 High-Risk HPV/Qiagen Inc. | HPV DNA (13 types) | DNA hybridization/ immunoassay | Chemiluminescence | Complex (multiple steps, skilled person, etc.) | No (qualitative) | 93% | Ca. 6.5 hours |
| CerMark™/CerMed Corporation | HPV and HPV-included proteins | Disc technology/ immunoassay | Electrochemical | Simple (no laboratory required) | Yes | More than ELISA | 15 minutes |
| Cervista™/Hologic, Inc. | HPV DNA (14 types) | DNA hybridization/ FRET | Fluorescence | Complex | No (qualitative) | 92.8% | - |
| AMPLICOR HPV Test/Roche | HPV DNA (13 types) | Amplification of target DNA by PCR | Colorimetry | Complex | No (qualitative) | 96.1% (analytical sensitivity) | - |

▲ Pap smear testing (cytology) or visual inspection with acetic acid (VIA), which are convention HPV testing methods
▲ VIA and Pap testing had clinical sensitivities of 41% and 85% respectively.

FIG. 3

| Test | Combined number of samples test | Sensitivity (%): median (Low-high range) | Specificity (%): median (Low-high range) | Protocol | Disadvantage in LMICs |
|---|---|---|---|---|---|
| p16INK4a+Ki67 (CINtec) | 4733 | 88 (59-96) | 63 (41-96) | IHC NOT POC | Need Morphology and pathology laboratory infrastructure Pathologist – same as Pap test |
| TOP2 MCM2 (ProEX C) | 1824 | 86 (67-99) | 75 (61-85) | IHC NOT POC | Same as above |
| E6/E7 mRNA (APTIMA) | 3509 | 33 (90-95) | 51 (42-61) | PNA-PCR NOT POC | Need TIGRIS DTS system and other equipment – care in collecting samples and trained personal |
| Xpert HPV, HC2, COBAS | Varies | 82-91 | 40-43 | DNA-PCR NOT POC | Same as above need lab infrastructure |

FIG. 6

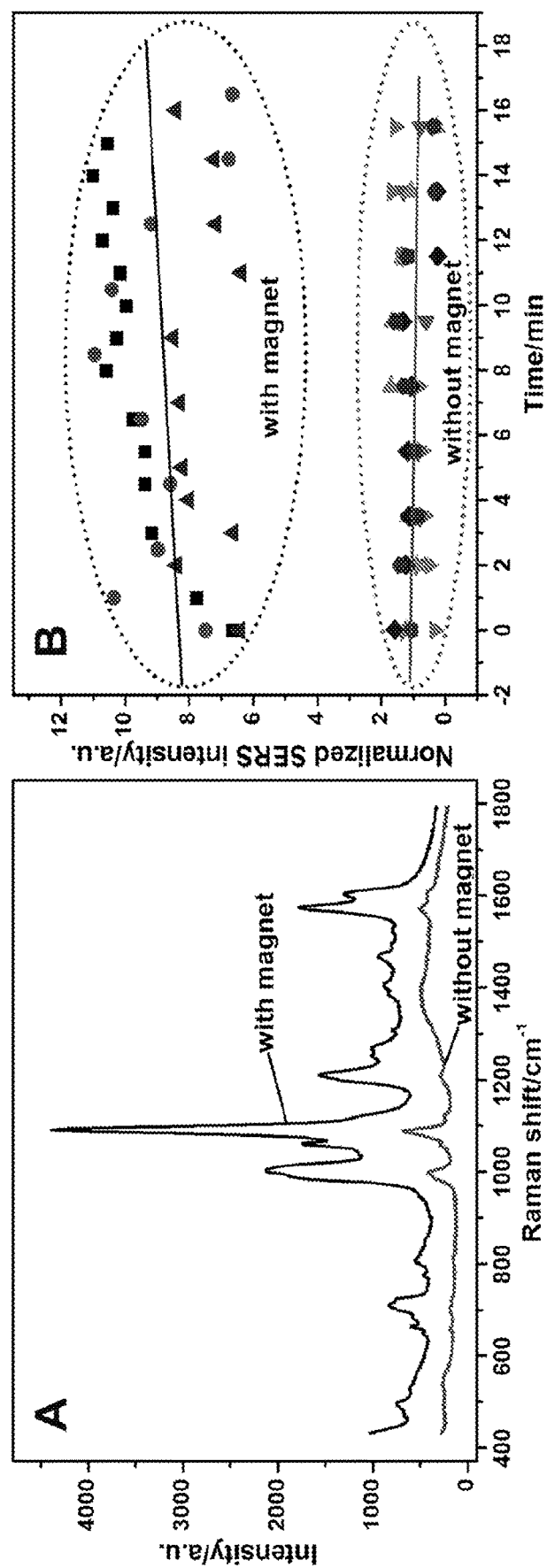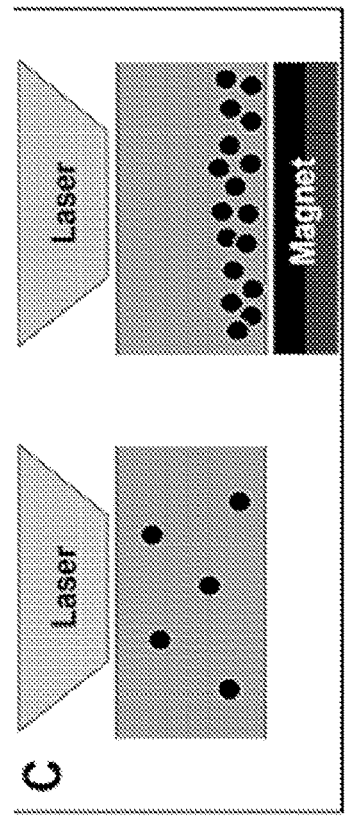
FIG. 22

DEVICES, SYSTEMS, AND METHODS FOR THE DETECTION OF A TARGET ANALYTE USING MAGNETIC FOCUS LATERAL FLOW IMMUNOASSAY TECHNIQUES

PRIORITY

This application is related to and claims priority benefit of U.S. Provisional Patent Application Ser. No. 62/361,089 to Irudayaraj filed Jul. 12, 2016. The entire content of the aforementioned priority application is hereby incorporated by reference in its entirety into this disclosure.

BACKGROUND

In most cases, cervical cancer is preventable and curable if detected early. Despite this, cervical cancer continues to claim many lives among relatively young women living in low- and middle-income countries (collectively, "LMICs") around the world. According to the International Agency for Research on Cancer (IARC), cervical cancer is the third most common cancer globally, following breast and colorectal cancers, and is the fourth most common cause of cancer death after breast, lung and colorectal cancers. In 2008 alone, it was estimated that 529,512 women were diagnosed with cervical cancer and about 274,967 women died of the disease. The majority of the cases diagnosed (about 85.5%) and deaths (about 87.9%) were in low-resource countries (see FIG. 1).

In Europe and the United States, where there are about 658.3 million women aged 15 years and older at risk of developing cervical cancer, around 146,465 women are diagnosed with cancer of the cervix, with only 57,248 (about 40%) dying from the disease. In comparison, of 267.9 million women in Africa that are in the at-risk group for developing cervical cancer (age 15 years and older), 80,000 women are diagnosed and 60,000 women die each year (about 75%), with the highest incidence and death rates occurring in Easter and Southern Africa (see FIG. 2). The wide disparity in cervical cancer incidence rates and death between LMICs and high-income countries is directly attributable to the implementation of national screening programs in high-income countries. Even as far back as 1986, results from the world screening data analyzed by IARC supported that well-organized screening programs were effective in reducing death from cervical cancer. Despite the clear indication of their efficacy, an organized, population-based cervical cancer screening program has yet to be implemented in LMICs for many reasons including limited resources, scarcities in trained personnel, and the lack of availability of appropriate screening tests.

The conventional cytology-based screening test (i.e. the Pap smear) has had a significant effect on morbidity and mortality rates among women living in high-income countries. The rationale behind the screening program is that lesions, such as cervical intraepithelial neoplasia grade-2 and -3 (CIN-2/3), and early cervical cancer progress slowly to invasive cancer (averaging 10 years or more). Using cytology, women are screened and those with abnormalities are referred for more evaluation with colposcopy and cervical biopsy. If cancer is found, women are treated immediately. While effective, conventional testing techniques require that a significant baseline healthcare infrastructure is in place to organize and implement each step of this process—namely, at least a trained cytologist/pathologist, a referring system, colposcopy and histopathological laboratories, a system and culture of follow-up (which could be as simple as women willing to come back, mail addresses, mail carrier infrastructure, reading ability, and language), and finally the ability to provide treatment. Unfortunately, a dedicated and highly skilled workforce of cytotechnologists and pathologists is not readily available in most LMICs, nor is the extensive clinical infrastructure for follow-up, evaluation, and treatment.

To overcome the limitations of implementing an effective screening program in an LMIC using the Pap smear test, two alternative tests have been developed—1) visual inspection with acetic (VIA); and 2) High Risk Human Papilloma Virus DNA (HR-HPV DNA) test. Primarily, the visual inspection with vinegar is inexpensive, simple, and a true point-of-care ("POC") test. A person with mid-level education can be employed to screen women. In brief, VIA is based on the fact that cervical intraepithelial neoplasia (CIN), grade 2 and 3 lesions, develop a white color when about five percent (5%) acetic acid or vinegar is applied to the cervical epithelium (called acetowhite), while a healthy cervix remains pink in color. Accordingly, women exhibiting acetowhite cervical lesions (i.e. test positive) may be either treated or referred for further evaluation.

However, while VIA testing is very simple and allows for immediate results and treatment, cervical cell acetowhitening is not specific. Conditions that are non-cancerous such as areas of immature squamous metaplasia or reparative conditions typically turn white upon acetic acid application as well, thus leading to considerable over referral and over treatment. These limitations led to the development of a number of criteria and comprehensive training courses to improve the specificity of VIA. In addition to this extensive training, the test performance significantly declines in women aged 40 years and older.

HPV-DNA/RNA tests have also recently been introduced as a cervical cancer-screening alternative that are bases on the understanding that infection with HR-HPV is required to induce transformation and cancer. Many versions of the HPV-DNA and RNA tests are now commercially available. For example, the Hybrid Capture 2 HPV-DNA Test is a 96-well microplate assay based on signal-amplified nucleic acid hybridization that uses chemiluminescence for the qualitative detection of 18 types of HPV-DNA in a cervical specimen.

Unfortunately, the HPV-DNA/RNA test is not POC and requires multiple visits at a great cost to the patient. Furthermore, the test is expensive, involves a cumbersome procedure, and requires sophisticated laboratory equipment. Even if a new POC version of the HPV-DNA/RNA test was developed, and assuming that all types of HPV for a particular population were known, it would only provide a test to identify women at risk, not the presence of cervical cancer. Indeed, most HPV infections resolve spontaneously and only very few infected women develop clinically relevant lesions. As such, one positive HPV test does not justify medical intervention in and of itself, but rather identifies women who have an elevated risk if the infection persists. Treatment of premalignant lesions with potential to spontaneously regress may lead to overtreatment with many side effects, emotional distress, and unnecessary cost. Furthermore, the potential to control infection by vaccination should reduce the incidence of HPV-associated neoplasia in the population and will likely change the way we performing screening in the future.

To overcome the limitations of conventional technologies and implement an effective and lifesaving screening program in LMICs, there is a need for an easy, efficient test that can accurately and affordably detect and diagnose cervical CIN-2/3 and/or cervical cancer in a patient and allow for immediate treatment, without the risk of significant over diagnosis which leads to over treatment.

BRIEF SUMMARY

Devices, systems, and methods are provided for magnetic focus enhanced lateral flow assays. The devices and systems are ultrasensitive and provide for the visual detection of the presence or absence of one or more target analytes—which may include pathogens, proteins, or even molecules smaller than the foregoing—even when such analytes are only present in very limited amounts. In at least one embodiment, an assay device is provided for detecting the presence or absence of one or more target analytes in a fluid sample. Here, the assay device comprises one or more strips of a porous substrate comprising a first conjugate area and a capture area in flow contact with the first conjugate area.

The first conjugate area may comprise one or more conjugates, each conjugate for binding a target analyte if present within a fluid sample to form a target analyte complex. Similarly, the capture area may comprise one or more immobilized capture ligands coupled thereto, each of the one or more immobilized capture ligands comprising an antibody or an aptamer specific to the target analyte. Significantly, the assay device further comprises at least one magnet positioned at or near the capture area of the one or more strips. The at least one magnet may be configured to magnetically interact with the target analyte complex to reduce a flow rate of said target analyte complex through the capture area. In at least one embodiment, the first conjugate area and the capture area may each support flow of the fluid sample along a first flow direction and generation of a signal in the capture area is indicative of a target analyte being present within the fluid sample.

The target analyte may comprise a protein or a microorganism. Additionally or alternatively, the target analyte may comprise a molecule smaller than a microorganism such as a polysaccharide molecule, a peptide, or the like. It will be appreciated that the devices and systems hereof may be configured as multiplex devices and, thus, be configured to test a single fluid sample for multiple target analytes in a single run. Likewise, the fluid sample tested by the assay devices hereof may comprise saliva, urine, blood, or cells suspended in a buffer solution. In at least one embodiment, the assay devices of the present disclosure comprise a limit of detection of less than 100 pg/ml of the fluid sample and, thus, exhibit an incredible amount of specificity and sensitivity heretofore unseen in the relevant arts.

In at least one exemplary embodiment of the assay device provided herein, the device may further comprise at least one supply area comprising a porous substrate positioned laterally of the capture area. There, the at least one supply area supports flow of an agent received thereon to the capture area along a second flow direction. The first flow direction and the second flow direction may cross each other, for example, the first flow direction may comprise vertical flow, whereas the second flow direction may comprise horizontal flow.

Additionally, the agent to be received upon the at least on supply area may be for generating a signal upon contact with a target analyte complex. In at least one exemplary embodiment, the agent may comprise an enzymatic substrate for generating a signal when in contact with a target analyte complex bound to the one or more immobilized capture ligands of the capture area. Such an enzymatic substrate can be tetramethyl benzidine and/or may be formulated to generate a colorimetric signal upon reaction with the conjugate of the target analyte complex.

The devices and systems hereof may optionally comprise a sample receiving area for receiving the fluid sample. There, the sample receiving area is in flow contact with the first conjugate area and supports flow of the fluid sample along the first flow direction.

In certain embodiments, the first conjugate area and the capture area each comprise a separate pad attached to a first side of an impermeable or hydrophobic barrier, with the optional receiving area and the first conjugate area positioned to overlap each other (where applicable) and the first conjugate area and the capture area positioned to overlap each other by, in at least one case, about 0.2 cm. Where an impermeable or hydrophobic barrier is employed, the at least one magnet may be affixed to a second side thereof.

The capture area (or at least a portion thereof) of the assay devices and systems of the present disclosure may comprise a low-flow membrane strip—such as a nitrocellulose membrane—with each of the one or more capture ligands tethered thereto.

In at least one exemplary embodiment, the magnet of the device is configured to exert an attractive magnetic field on the target analyte complex. Additionally or alternatively, the at least one magnet may be further configured to exert a magnetic field on the target analyte complex to focus flow of the target analyte complex to a specified position in the capture area (e.g., such as a concentration of capture ligands).

As previously noted, the first conjugate area comprises one or more conjugates. In at least on embodiment, the one or more conjugates comprises an enzyme-catalyzed tracer such as horseradish peroxidase, for example. In at least one exemplary embodiment, the enzyme-catalyzed tracer further comprises a streptavidin construct having at least one horseradish peroxidase molecule chemically coupled thereto.

Still further, the devices and systems hereof may further comprise a second conjugate area, a third conjugate area, etc., each of the additional conjugate areas supporting flow of the liquid sample between the adjacent areas in the first flow direction towards the capture area.

As previously stated, at least one embodiment of the assay devices of the present disclosure is configured to be a multiplex assay. In at least one embodiment of such a multiplex assay, at least one of the one or more immobilized capture ligands comprises an antibody or an aptamer specific to a first target analyte that, upon binding a first target analyte complex formed between the conjugate and the first target analyte, immobilizes the first target analyte complex at a first attachment site. Furthermore, in such cases, the conjugate of the first target analyte complex generates a first signal at the first attachment site upon contact with an enzymatic substrate. In addition, at least one of the one or more immobilized capture ligands may comprise an antibody or an aptamer specific to a second target analyte that, upon binding a second complex formed between the conjugate and the second target analyte, immobilizes the second target analyte complex at a second attachment site. Additionally, the conjugate of the second target analyte complex generates a second signal at the second attachment site upon contact with an enzymatic substrate, and visibility of the first signal is indicative of the first target analyte being present within the fluid sample and visibility of the second signal is indicative of second target analyte being present within the fluid sample.

Still further, the multiplex assay may be configured to also test for a third target analyte, a fourth target analyte, or any additional number of target analytes as may be necessary or desired for a particular application. For example, where the multiplex assay is configured to test for four separate target analytes, in addition to the previously described, at least one of the one or more immobilized capture ligands of the assay device may comprise an antibody or an aptamer specific to the third target analyte that, upon binding a third target analyte complex formed between the conjugate and the third target analyte, immobilizes the third target analyte complex at a third attachment site and the conjugate of the third target analyte complex may generate a third signal at the third attachment site upon contact with an enzymatic substrate. Further, at least one of the one or more immobilized capture ligands may comprise an antibody or an aptamer specific to a fourth target analyte that, upon binding a fourth complex formed between the conjugate and the fourth target analyte, immobilizes the fourth target analyte complex at a fourth attachment site upon contact with an enzymatic substrate, the conjugate of the fourth target analyte complex may generate a fourth signal at the fourth attachment, and visibility of the third signal is indicative of the third target analyte being present within the fluid sample and visibility of the fourth signal is indicative of the fourth target analyte being present within the fluid sample.

Methods for identifying the presence of a target analyte in a fluid sample the method comprising: adding a probe comprising a magnetic nanoparticle to a fluid sample collected from a subject, the probe for labeling the target analyte; tethering a conjugate to a labeled target analyte present within the fluid sample to form a target analyte complex; receiving the fluid sample on an assay device and allowing the fluid sample to flow in a first direction for immunocomplex formation between the target analyte complex present within the fluid sample and an immobilized capture ligand; and controlling movement of the target analyte complex in the capture area of the assay device using a magnetic field generated between the at least one magnet of the assay device and the magnetic nanoparticle of the target analyte complex; wherein generation of a signal is indicative of the presence of the target analyte within the fluid sample. In such cases, the target analyte may comprise a microorganism, a protein, or a molecule smaller than a microorganism such as, without limitation, a polysaccharide molecule or a peptide. Furthermore, the immobilized capture ligand may comprise an antibody or aptamer specific to the target analyte.

In at least one exemplary embodiment, the method may further comprise initiating a flow of an agent in a second flow direction through at least one supply area of the assay device for colorimetric signal generation at a site of immunocomplex formation, the second flow direction intersecting the first flow direction.

Still further, the methods of the present disclosure may optionally comprise the step of washing the capture area with a fluid to remove any unbound conjugates or probes. Additionally or alternatively, such methods may further comprise quantifying the colorimetric signal present on the capture area. There, in at least one embodiment, quantifying further comprises capturing an image of the colorimetric signal present on the capture area; and analyzing the image to identify a coloration value and a light intensity value of the colorimetric signal; wherein the light intensity value is indicative of a concentration of the target analyte within the fluid sample. The step of analyzing the image may be performed by a software application run on a microprocessor or the like. Alternatively, the step of analyzing may be performed by a software application based and/or run from a cloud-based server. In at least one embodiment, the software application comprises a mobile application and the camera comprises a camera integral with a mobile phone. The software application may employ calibration standards and peak and curve analysis programs in analyzing the image.

Tethering a conjugate to a labeled target analyte present within the fluid sample may be performed in a first conjugate area of the assay device, the first conjugate area comprising the conjugate. Additionally or alternatively, the magnetic field may comprise an attractive magnetic field and/or controlling movement of the target analyte complex in the capture area may further comprise reducing a flow rate of the target analyte complex through the capture area of the assay device.

The agent utilized in the method may comprise tetramethyl benzidine and, in such cases the signal may be a colorimetric signal and the conjugate may comprise an enzyme-catalyzed tracer. An exemplary embodiment of one such enzyme-catalyzed tracer comprises a streptavidin construct having at least one horseradish peroxidase molecule chemically coupled thereto.

The probes of the method may comprise a biotinylated gold-based magnetic nanoparticle modified with an aptamer or antibody specific to a target analyte. For example, in certain embodiments, the probe may comprise a monoclonal antibody with high affinity for a target analyte or an aptamer specifically designed for a target analyte. The biotinylated gold-based magnetic nanoparticle may be spherical, comprise a ferroferric oxide nanoparticle core within a gold shell, and/or the gold shell may be coated in spatially controlled biotin-containing chemical cross linkers. Furthermore, in certain embodiments, the biotinylated gold-based magnetic nanoparticle further comprises one or more spacers and/or may be between 20 nm and 50 nm in diameter. Still further, the magnetic nanoparticle of the probe may comprise a 40 nm diameter and at or about 73 spatially controlled biotin-containing chemical cross linkers; the conjugate may comprise an enzyme-catalyzed tracer; and when the enzyme-catalyzed tracer is bound to the magnetic nanoparticle, the target analyte complex may comprise at or about 219 horseradish peroxidase molecules bound to the chemical cross linkers of the nanoparticle.

Depending on the desired application of the method, the probe may comprise a primary antibody or aptamer specific to the first target analyte and a secondary antibody or aptamer specific to the first target analyte.

As with the devices and systems of the present disclosure, the target analyte may comprise a biomarker for cervical cancer or a biomarker for an infection of the cervix and the presence of the target analyte in the fluid sample is indicative of the subject either being at risk for or experiencing cervical cancer or an infection of a cervix. Alternatively, the target analyte may comprise a protein that is selected from a group consisting of: a valosin-containing protein, a minichromosome maintenance protein 2, a topoisomerase II alpha, a cyclin-dependent kinase inhibitor 2A, an E6 protein, an E7 protein or another Human Papillomavirus oncoprotein. There, if the fluid sample comprises cells collected from a subject and a signal is generated, the signal is indicative of the subject being at risk for or experiencing cervical cancer or an infection of a cervix. Still further, the target analyte may comprise *Salmonella typhimurium, Escherichia coli*, or *Listeria monocytogenes* and, in such cases, if the fluid sample comprises cells collected from food matter and a signal is generated, such signal is indicative of the food matter being contaminated with the target analyte.

Sampling kits are also provided for point-of-care and other screening for the presence of a target analyte. In at least one exemplary embodiment, such a kit comprises one or more strips of a porous substrate comprising: a first conjugate area comprising one or more conjugates, each conjugate for binding a target analyte if present within the fluid sample to form a target analyte complex, a capture area in flow contact with the first conjugate area and comprising one or more immobilized capture ligands coupled thereto, each of the one or more immobilized capture ligands comprising an antibody or an aptamer specific to the target analyte, and at least one magnet positioned at or near the capture area of the one or more strips, wherein the first conjugate area and the capture area each support flow of the fluid sample along a first flow direction and generation of a signal in the capture area is indicative of the target analyte being present within the fluid sample; a plurality of magnetic probes for labeling the target analyte present within a fluid sample; and an agent for signal generation upon contact with a site of immunocomplex formation. Such components of the kits may comprise any of the various probes, agents, analytes, devices, conjugates, etc. that are described herein in connection with the various embodiments of the present disclosure. Additional embodiments of the kit may further comprise a swab for collecting a tissue sample from a subject; and a container for suspending the tissue sample in a liquid. Additionally or alternatively, the sampling kit may also comprise an amount of distilled water.

Still further, application-specific assay devices are provided. In at least one embodiment, such an assay device is configured for detecting the presence or absence of one or more target proteins indicative of cervical cancer or a vaginal infection in a liquid sample. There, the assay device may be configured similar to those embodiments previously described. For example, such an assay device may comprise: one or more strips of a porous substrate comprising a first conjugate area comprising one or more conjugates, each conjugate for binding the target protein if present within a liquid sample to form a target protein complex, and a capture area in flow contact with the first conjugate area and comprising one or more immobilized capture ligands coupled thereto, each of the one or more immobilized capture ligands comprising an antibody or an aptamer specific to the target protein; and at least one magnet positioned at or near the capture area of the one or more strips, the at least one magnet configured to magnetically interact with the target protein complex to reduce the flow rate of the target protein complex through the capture area; wherein the first conjugate area and the capture area each support flow of the liquid sample along a first flow direction and generation of a signal in the capture area is indicative of a target protein being present within the liquid sample and the patient being at risk for or experiencing cervical cancer or an infection of a cervix. Additionally, in at least one exemplary embodiment the assay device may comprise at least one supply area comprising a porous substrate positioned laterally of the capture area, the at least one supply area for supporting flow of an agent received thereon to the capture area along a second flow direction, the agent for generating a signal upon contact with a target protein complex. There, the at least one supply area may further comprise an agent comprising an enzymatic substrate that enhances a signal generated by the one or more immobilized capture ligands of the capture area, and the enzymatic substrate comprises tetramethyl benzidine and is formulated to generate a colorimetric signal upon reacting with the conjugate of the target protein complex. In at least one iteration, the target protein comprises a valosin-containing protein, a minichromosome maintenance protein 2, a topoisomerase II alpha, a cyclin-dependent kinase inhibitor 2A, an E6 protein, an E7 protein, or another Human Papillomavirus oncoprotein. Perhaps less specifically, the target protein may comprise a biomarker for cervical cancer or a biomarker for an infection of a cervix.

Other application specific assay devices are also provided; in at least one exemplary embodiment, an assay device is provided for detecting one or more foodborne pathogens. There, the device may comprise one or more strips of a porous substrate comprising: a first conjugate area comprising one or more conjugates, each conjugate for binding a target pathogen if present within a liquid sample to form a target pathogen complex, and a capture area in flow contact with the first conjugate area and comprising one or more immobilized capture ligands coupled thereto, each of the one or more immobilized capture ligands comprising an antibody or an aptamer specific to the target pathogen; and at least one magnet positioned at or near the capture area of the one or more strips, the at least one magnet configured to magnetically interact with the target pathogen complex to reduce a flow rate of the target pathogen complex through the capture area; wherein the first conjugate area and the capture area each support flow of the liquid sample along a first flow direction and generation of a signal in the capture area is indicative of the target pathogen being present within the liquid sample. Furthermore, in at least one exemplary embodiment, the device may further comprise at least one supply area comprising a porous substrate positioned laterally of the capture area, the at least one supply area supporting flow of an agent received thereon to the capture area along a second flow direction, the agent for generating a signal upon contact with the target analyte complex. There, the liquid sample may comprise cells collected from a food to be tested suspended in a buffer solution or blood, urine, or saliva collected from a patient. Additionally or alternatively, the target pathogen may comprise *Salmonella typhimurium*, *Escherichia coli*, or *Listeria monocytogenes*.

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 3 shows a table of conventional cervical cancer marker kits available from selected vendors;

FIG. 6 shows a table displaying the sensitivity, specificity, protocol and disadvantages of commercially available tests to detect various biomarkers in comparison to HPV tests;

FIG. 22 depicts the results of a SERS characterization of magnetic nanoparticle distribution in the micro-channel of FIG. 21, with A) showing a SERS signal after 15 minutes following sample addition; B) showing the normalized SERS intensity according to time and corresponding linear fit; and C) showing a scheme of the magnetic field of influence on the magnetic nanoparticle distribution in microchannel, supporting that increased particles are seen with a magnetic field as expected;

Figure 1:
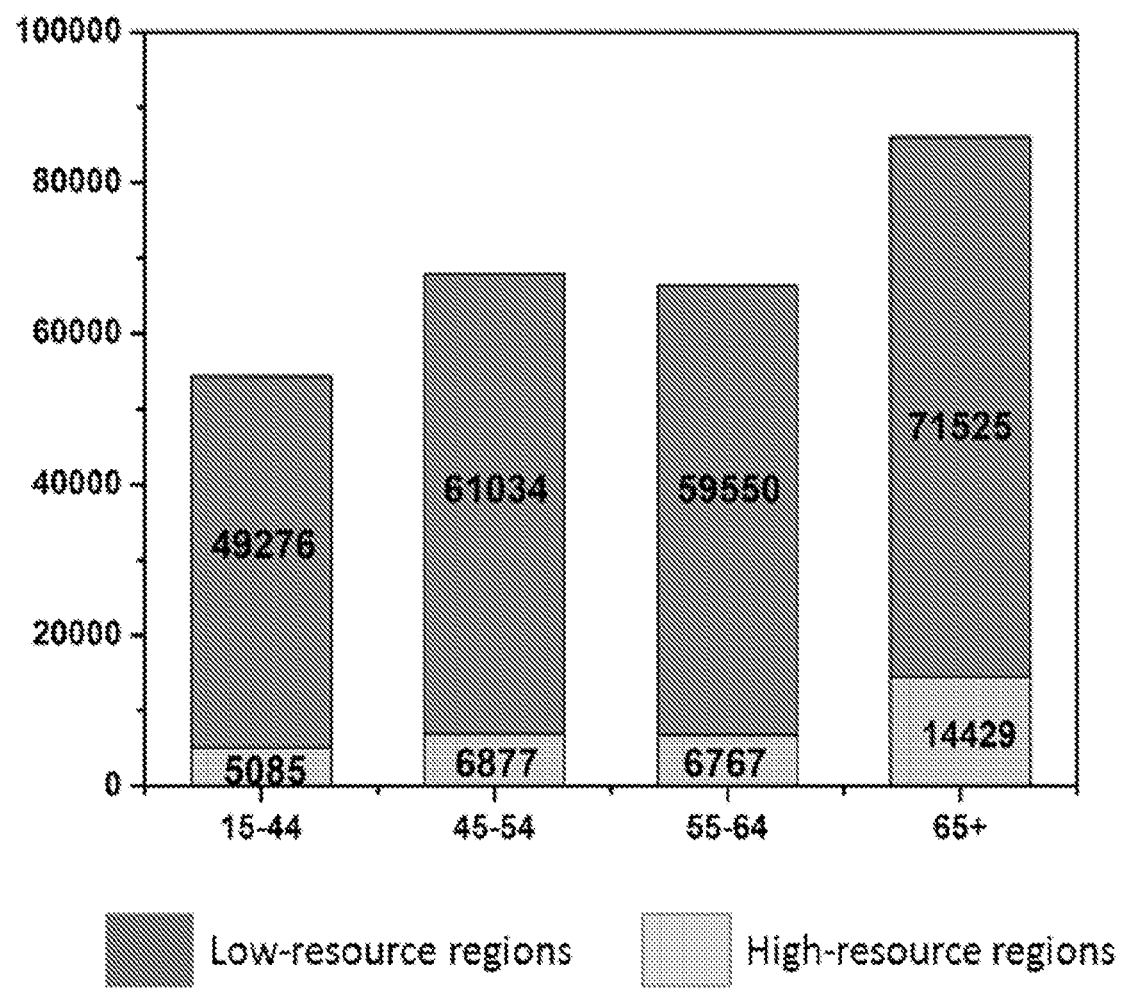
FIG. 1 shows a bar graph representative of the annual number of deaths from cervical cancer by age group in high- and low-resource regions around the world.
Figure 2:
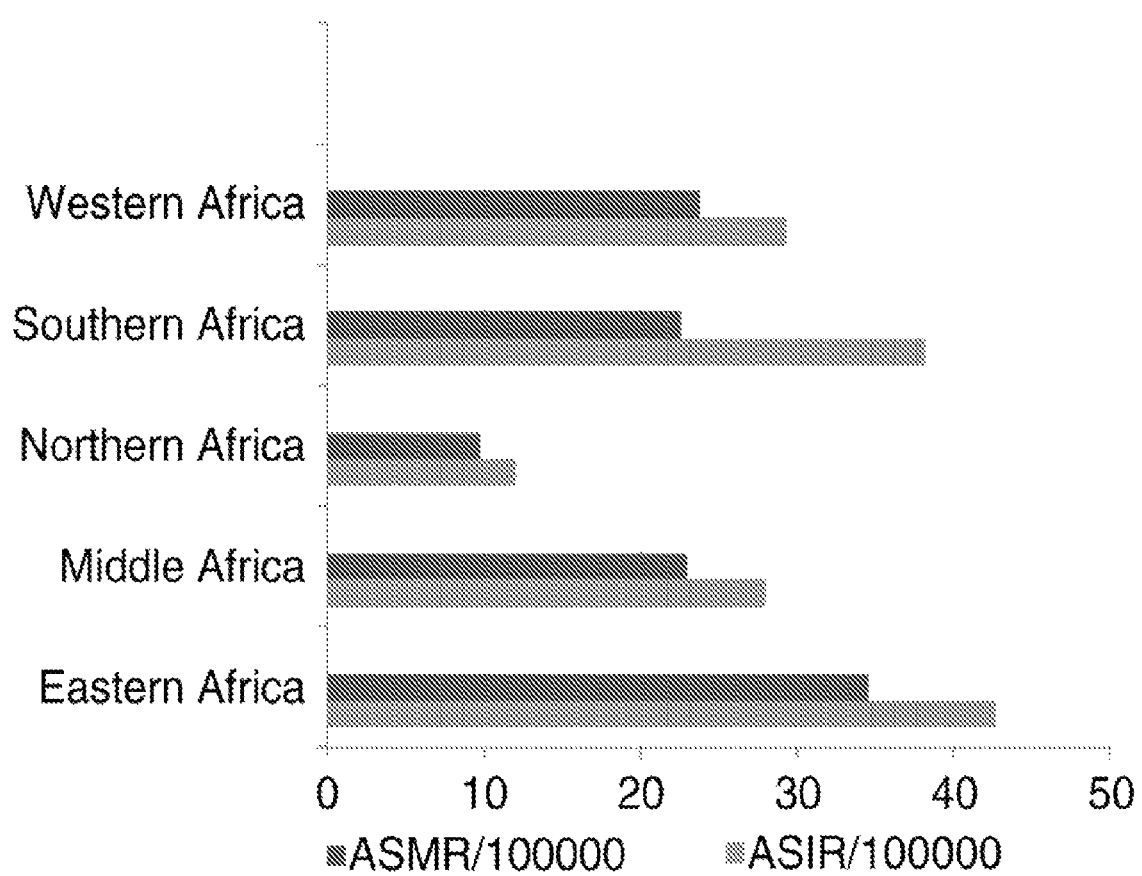
FIG. 2 shows a bar graph showing the age-standardized incidence rate (ASIR) per 100,000 and the age-standardized mortality rate (ASMR) per 100,000 of cervical cancer in different regions of Africa.

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Furthermore, unless specifically stated otherwise, the term "about" refers to a range of values plus or minus 10% for percentages and plus or minus 1.0 unit for unit values, for example, about 1.0 refers to a range of values from 0.9 to 1.1.

As used herein, the term "microorganisms" means any microscopic organisms, including without limitation a bacterium, virus, or a fungus. Likewise, the term "pathogen" as used in the present disclosure means any type of bacterium, virus, or other microorganism that can cause disease.

A "subject" or "patient" as the terms are used herein is a mammal, preferably a human, but can also be an animal. Furthermore, in connection with foodborne pathogen applications of the technology provided herein, a "subject" may also be read to include food matter.

As used herein, the term "therapeutically effective dose" means (unless specifically stated otherwise) a quantity of a compound which, when administered either one time or over the course of a treatment cycle affects the health, wellbeing or mortality of a subject (e.g., and without limitation, delays the onset of and/or reduces the severity of one or more of the symptoms associated with an active infection or cervical cancer). The amount of the compound to be administered to a recipient will depend on the type of disease being treated, how advanced the disease pathology is, and the characteristics of the patient or subject (such as general health, age, sex, body weight, and tolerance to drugs).

A "marker" or "biomarker" as the terms are used herein may be described as being differentially expressed when the level of expression in a subject who is experiencing an active disease state is significantly different from that of a subject or sample taken from a healthy subject. A differentially expressed marker may be overexpressed or underexpressed as compared to the expression level of a normal or control sample or subjects' baseline. The increase or decrease, or quantification of the markers in a biological sample may be determined by any of the several methods known in the art for measuring the presence and/or relative abundance of a gene product or transcript. The level of markers may be determined as an absolute value, or relative to a baseline value, and the level of the subject's markers compared to a cutoff index. Alternatively, the relative abundance of the marker or markers may be determined relative to a control, which may be a clinically normal subject.

As used herein the terms "detection limit," "limit of detection," or "LOD" means the lowest concentration or quantity of a substance that can be reliably measured by an analytical procedure.

As used herein, the term "point of care" or "POC" means the point in time when clinicians or other healthcare providers delivery healthcare products and services to patients at the time of care. Diagnostic testing that occurs at POC is performed at or near the point of care/bedside (as compared to historical testing which was wholly or mostly confined to the medical laboratory—i.e. sending specimens away).

To overcome the limitations of implementing an effective screening program in an LMIC, the present disclosure provides novel devices, systems, and methods or use for diagnosing cervical cancer. Almost all LMICs have the lowest Human Development Index and Highest Poverty Indices and most lack cancer registries and access to anti-cancer therapy. In such countries, most patients that seek clinical assistance present with advanced disease and about 78% of those diagnosed with cancer die from it.

For example, in sub-Saharan Africa, patient survival rate is extremely low. About 15 countries in Africa have no radiotherapy facilities. In countries where radiotherapy facilities are available, they are often nonfunctional or poorly maintained. Furthermore, other challenges such as environmental disasters, communicable diseases, endemic civil strife, war, lack of safe water and sanitation, and the HIV/AIDS epidemic all compete for the already meager country resources. Accordingly, for the adoption of a diagnostic device and/or therapy to be successful, it necessarily must be low cost and affordable, with limited or no need for laboratory equipment, electricity, or extensive clinical infrastructure. The devices, systems, and methods hereof satisfy all such criteria.

Furthermore, there is a great shortage of trained healthcare personnel in LMICs. Pathology and surgery services can be a barrier to cancer care in LMICs and may lead to delay in diagnosis and/or result in misdiagnosis that adversely affect patient care and survival. High-income countries, such as the United States and Canada (about 14% of the world population) spend about 50% of all the world's healthcare dollars and employ about 37% of the global health care workforce to address only 10% of the world's disease burden. This greatly contrasts with Sub-Saharan Africa (11% of the world's population), which spends only 1% of the world's dollars and employs only 3% of the global health workforce to address 24% of the world's disease burden. For example, the ratio of physicians per 1,000 individuals is 0.02 in Tanzania and 0.04 in Chad, as compared with 2.14 in Canada and 2.56 in the United States. According to the WHO, this disparity is caused by past investment shortfalls in pre-service training, international immigration, career changes among health workers, premature retirement, morbidity, and premature mortality. Beneficially, the embodiments of the devices, systems, and methods disclosed herein do not require pathologists or sophisticated, trained professionals; instead, an individual with mid-level training can perform and interoperate the test.

To provide perspective, FIG. 3 illustrates a variety of test kits for cervical cancer that are conventionally available. Most are based on HPV evaluation, which is insufficient for a variety of reasons previously discussed.

The present disclosure provides novel devices, systems, and methods for the rapid screening of proteins, pathogens (including, without limitation, bacteria, viruses, or other microorganisms) and other target analytes smaller than the foregoing. The novel approaches described herein provide at least a 100-fold enhancement as compared to even the most efficient conventional kits available. Indeed, due to the surprising and heretofore unavailable sensitivity of the presently disclosed devices, systems, and methods, even smaller analytes, such as polysaccharide molecules and peptides, can be accurately and quickly detected in a sample. In addition, the novel devices, systems, and methods hereof can accurately detect a target analyte within a sample even when the target analyte is only present in a very low amount or concentration. Without being bound by any particular theory, the inventive application of magnetic focus to slow down the movement of the target analyte as it flows through a capture area of an immunostrip increases target capture efficiency and plays an important role in the success rate of sensitivity. Given that the devices and systems may be prepared for point-of-care application, may be disposable, and are easy to use with accuracy, this unprecedented sensitivity has numerous important clinical and/or commercial applications.

Generally, the novel approaches presented herein comprise an improved lateral flow immunoassay sensor with a magnetic focus that, due to a unique enhancement from gold nanoparticles (AuNP) and horseradish peroxidase ("HRP") enzyme labels, allows for ultrasensitive naked-eye detection at or near a single cell limit. This can be achieved without any pre-enrichment steps by allowing the magnetic probes to focus the labelled target analytes to the target zone of the lateral flow strip. Furthermore, through the use of secondary AuNPs, additional enzyme labels can be tethered to the bioactive complex resulting in at least a 400-fold specificity enhancement.

Lateral Flow Immunochromatography (LFIA)

The technology underlying the novel devices, systems, and methods hereof is based on the principle of Lateral Flow Immunochromatography (LFIA) and manufactured using various innovative chromatographic immunoassay technologies—namely the Cross Lateral Flow-IC Platform and the magnetic Lateral Flow-IC Platform—which can yield over 100-fold enhancement compared to the conventional systems known in the art (and potentially over 400-fold enhancement) and allows for rapid diagnostic testing.

LFIA is a practical, simple, and cost-effective technique for rapid screening of pathogens. As a point-of-care ("POC") analytical method, LFIA sensors have been used to detect the presence (or absence) of target analytes with visual signals using the naked eye. In LFIA, a porous membrane strip is utilized as the immunosorbent (e.g., antibody or aptamers or peptide sensors that bind to a specific target or analyte of interest) to detect analytes present in biological samples applied to the strip such as blood, urine, and saliva. In principle, the concept is based on a series of pads (membrane strips), with a sample introduced at the first strip migrating to interact with the bioactive conjugates in the subsequent pad and subsequently captured at the signal generation pad.

Generally, lateral flow through the immunostrip may comprise different types of membranes to expedite the reaction, allowing for results in a relatively short time and further enabling the in situ separation of unreacted components via a one-step analysis. Usually, LFIA can be performed within fifteen (15) minutes by untrained personnel. Another key advantage of this format in that it allows for a user to monitor the reaction with the naked-eye, which facilitates ease-of-use and makes it valuable for on-site monitoring. Since the initial launch of a home pregnancy test utilizing LFIA, this simple and powerful technology has been employed to detect target analytes from various specimens for healthcare.

However, a key limitation of conventional LFIA systems is the lack of high sensitivity. Such tests are less sensitive than those associated with other conventional immunological methods, particularly enzyme-linked immunosorbent assay (ELISA). The limit of detection ("LOD") of conventional LFIA is in the range between $10^4$-$10^6$ CFU per ml for whole pathogen detection. This lack of sensitivity is insufficient when applied to applications such as the assessment of disease biomarkers (and particularly cancer markers) where quantitative analyses for early diagnosis and progress monitoring are classically constrained because of the low level of the markers present.

Several attempts have been made to improve the sensitivity of lateral flow approaches; however, these attempts have either resulted in little success or have proven to not be clinically or commercially viable. For example, while fluorescent probes have been employed to facilitate detection at lower LODs, this approach requires extra instrumentation to obtain a signal readout, as well as additional steps such as preculture enrichment and amplification of the DNA/RNA extracted from the targeted pathogens. Additionally, indicator analytes for bacteria such as intercellular enzymes or environmental chemicals consumed by viable bacteria have been used in LF-based detection to improve sensitivity, yet this approach increases the detection time needed.

Inspired by horseradish peroxidase (HRP) enhanced LF detection of DNA and protein, previous efforts have also introduced an enzyme amplification strategy. There, the HRP-catalyzed reaction was able to achieve a LOD of about 100 CFU per ml, however, this LOD remains too high to be clinically and/or commercially useful with respect to most pathogens. One of the principal reasons for poor sensitivity of the conventional LFIA platform is the limited interaction between the probe-labelled pathogens/analytes with the capture antibodies immobilized at the detection zone due to the low surface reaction rate. Since the flow through the LF strips is due to capillary action, the movement of labelled pathogens/analytes is governed by the material characteristics. As such, it is difficult to control how long the labelled targets are able to interact with capture antibodies. In conventional systems, this inevitably allows for a very limited duration of interaction between the target and capturing probe, which ultimately results in a low ratio of captured targets.

To overcome this critical weakness, isotachophoresis (ITP), an electrophoretic technique that can pre-concentrate and control the movement of the target by tuning the current, has also been applied. Slowing down the movement of the target using ITP allows for an increased interaction time between the elements and the LOD of the LFIA system. However, controlling the electric current in the strips requires additional instrumentation and, thus, limits the simplicity of the LFIA. In other efforts, the pattern and/or shape of LF strips themselves have been modified in hopes of reducing flow speed therethrough and prolonging reaction time. For example, a wax pillar pattern has been printed onto the LF strips in an attempt to utilize the pseudo-turbulence flow effect and LF strips having different shapes have also been employed. Despite these simple strategies, any improvement in LOD that resulted was not sufficiently significant to notably increase the sensitivity and allow for the detection of a target present in a low concentration.

In at least one exemplary embodiment of the present disclosure, a novel ultrasensitive magnetic-focus LFIA (mLFIA) technique is provided. Perhaps more specifically, the inventive concepts of the present disclosure utilize gold-based magnetic nanoparticles and, in certain embodiments, HRP in a novel cross-flow LFIA format to achieve an enhancement in sensitivity of over 100-fold to form the basis for a visual POC detection tool.

Figure 4A:
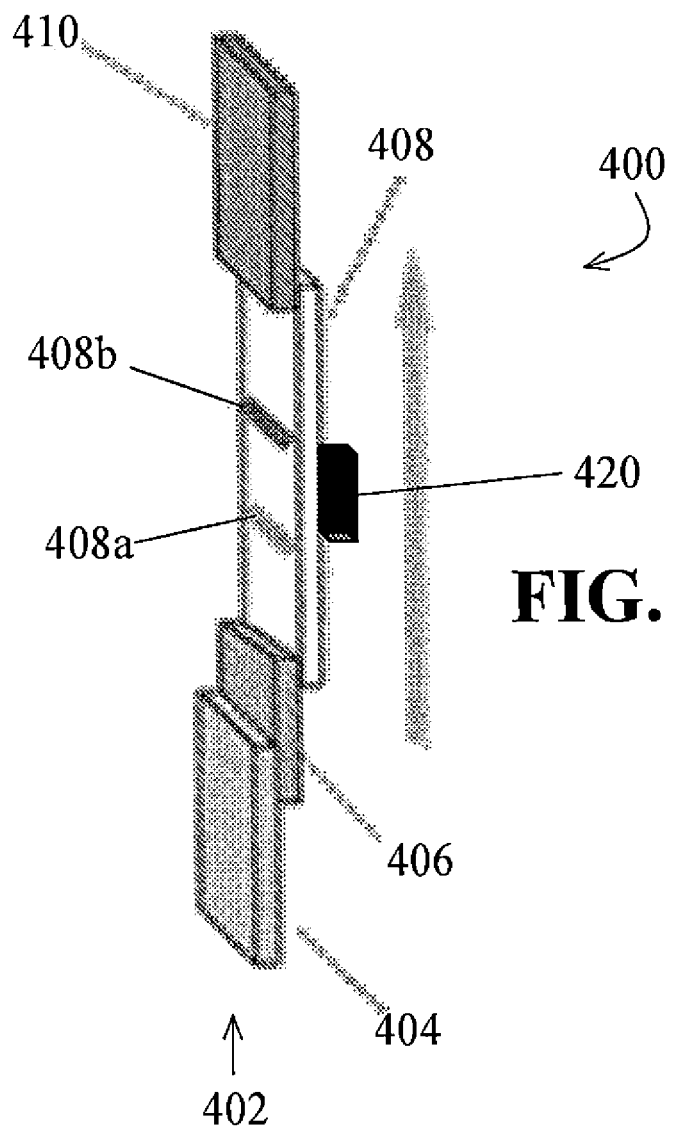
FIG. 4A illustrates an exemplary embodiment of the assay device of the present disclosure.
Figure 4B:
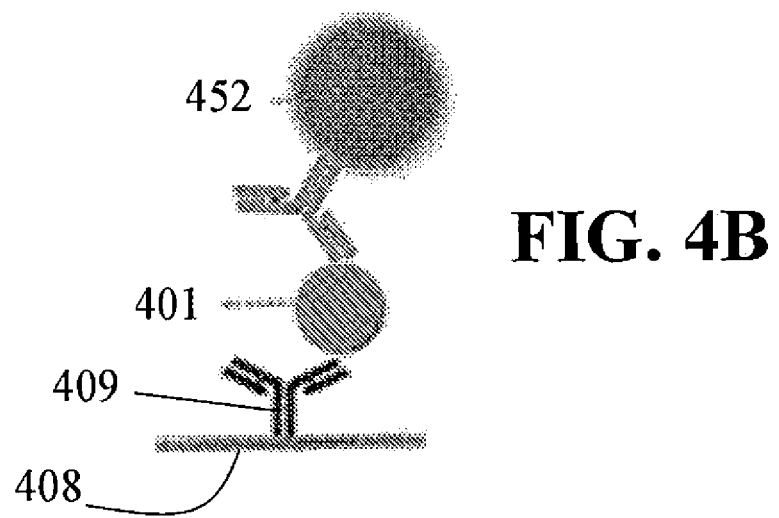
FIG. 4B shows an exemplary embodiment of a target analyte bound with an AuNP conjugate and a capture ligand at the signal generation site on the assay device of FIG. 4A.

Now referring to FIGS. 4A and 4B, a representation of at least one embodiment of an exemplary mLFIA device 400 of the present disclosure is shown. The mLFIA device 400 is configured to employ magnetic focus in detecting the presence or absence of one or more target analytes 401 in a fluid sample and exhibits significantly increased sensitivity and specificity over conventional devices and methods. Indeed, the novel use of a magnetic field to facilitate a focused interaction between the capture reagents and the target analytes has resulted in unprecedented results.

The mLFIA device 400 is ultrasensitive and may be a manufactured as a POC device and/or be disposable. Furthermore, the mLFIA device 400 enables a user to test a fluid sample for one or more target analytes 401 without specialized reading equipment—indeed, results on the device 400 may be interpreted and/or quantified with the naked eye and/or through the use of a simple mobile application (which is described in additional detail below). Compared with conventional methods based on LFIA, the present approach is rapid and simple, requiring no pre-enrichment or preculture steps.

The fluid sample may comprise any liquid that may contain one or more target analytes for consideration including, for example blood, saliva, or urine. Furthermore, a fluid sample may comprise cells that were swabbed or otherwise collected from a subject (whether mammal, food matter, or otherwise) and suspended in a buffer or similar solution (e.g., PBS solution). Additionally, due to the surprising sensitivity and specificity of the device 400, a number of different analytes 401 can be accurately detected thereby. For example, in at least one embodiment, the device 400 can detect proteins, microorganisms (including, but not limited to pathogens), and even smaller molecules such as a polysaccharide molecule or a peptide.

In at least one embodiment, the highly sensitive mLFIA device 400 comprises a strip 402 and at least one magnet 420. The inclusion of the magnet 420 slows down and/or focuses labelled target analytes 401 at the detection zone of the strip 402, thereby resulting in prolonged reaction time and a stronger signal when a target analyte is present within the fluid sample. This strategy overcomes the limitation of low surface reaction previously seen between microorganisms and proteins with capture antibody in conventional LFIA systems.

The strip 402 of the mLFIA device 400 comprises a porous substrate, a pad (or a series of pads) comprising a series of capillary beds or a flow matrix, a microstructured polymer, and/or the like. In any event, the strip 402 comprises the capacity to transport fluid spontaneously (i.e. achieve a flow of fluid applied thereto) along a first direction (see the arrow in FIG. 4A; here, the sample is shown flowing vertically along the strip 402 from its proximal end towards its distal end). While the strip 402 shown in FIG. 4 is depicted as a series of interconnected pads, it will be appreciated that the strip 402 may be a single strip or porous substrate, or alternatively comprise any number of strips, pads, polymers, etc. coupled together, provided that the appropriate areas of the device 400 are in flow contact with each other as described herein. In at least one embodiment, the strip 402 comprises a series of pads positioned to overlap each other as shown in FIG. 4A, with the overlap comprising at or about 0.2 cm.

The strip 402 may comprise a sample receiving area 404, one or more conjugate areas 406, a capture area 408, and an absorbent area 410. Furthermore, the strip 402 may be positioned on a first side of a hydrophobic or impermeable barrier 403 (see FIG. 7A). For example, and without limitation, the barrier 403 may be a plastic backing card or the like in the size of 6.0 cm×0.5 cm.

The sample receiving area 404 is optional and, in at least on embodiment, comprises the place on the device 400 where the sample to be tested is initially deposited and initiates migration to the other areas 406, 408, 410 of the strip 402. As such, the sample receiving area 404 may be configured to act as a sponge or the like to hold any excess fluid from the sample. Where employed, the sample receiving area 404 is in flow contact with the one or more conjugate areas 406 such that the fluid sample can easily flow thereto along the first direction.

The device 400 may comprise any number of conjugate areas 406 that store any number and/or types of conjugates. It will be appreciated that the number of conjugates areas 406 and number and variety of different conjugates used may be adapted as desired for the intended application. The embodiment of the mLFIA device 400 shown in FIG. 4A comprises one conjugate area 406.

The conjugates stored within the conjugate area(s) 406 may be any type, number or variety of conjugates for binding or reacting with one or more target analytes 401 present within the fluid sample. For example, the conjugates may comprise a dried format of bioactive particles in a salt-sugar matrix or as is otherwise known in the art. Additionally, multiple conjugates may be used, each for different purposes and/or to achieve the desired or optimized reaction between the conjugate(s) and the target analyte 401. In this manner, as the fluid sample flows through the conjugate area(s) 406, the conjugate(s) will bind any target analyte(s) 401 present therein while migrating further through the strip 402 (assuming the conjugates are specific to such target analytes or generally reactive).

As previously noted, to facilitate the magnetic interaction between the magnet 420 and the target analyte(s) 401 in the capture area 408, the target analyte(s) 401 are labelled with magnetic probes 452 that comprise gold-based magnetic nanoparticles (mNPs). Such magnetic probes 452 may be one of the conjugates in the conjugate area 406 of the mLFIA device 400 or, additionally or alternatively, the gold-based mNPs may be mixed with the fluid sample prior to application to the strip 402. These probes 452 may be prepared based on $Fe_3O_4$-Au core-shell nanostructures based on the methods reported below. Furthermore, the $Fe_3O_4$-Au core-shell nanostructures may be functionalized with biotin and modified with an antibody or aptamer against the target analyte 401.

Conjugates of the conjugate area(s) 406 may also include an enzyme-catalyzed tracer such as HRP and/or biotinylated gold nanoparticles. Enzyme-catalyzed tracers such as HRP are particularly useful in that the signals obtained from the mLFIA device 400 will be directly proportional to the amount of the enzyme participating in the reaction. In this mLFIA device 400, the enzyme-catalyzed reaction (a feature distinct from those of other tracers) may be conducted separately for enhanced signal generation following the completion of antigen-antibody-binding reactions in the capture area 408 (described in further detail below).

Figure 7A:
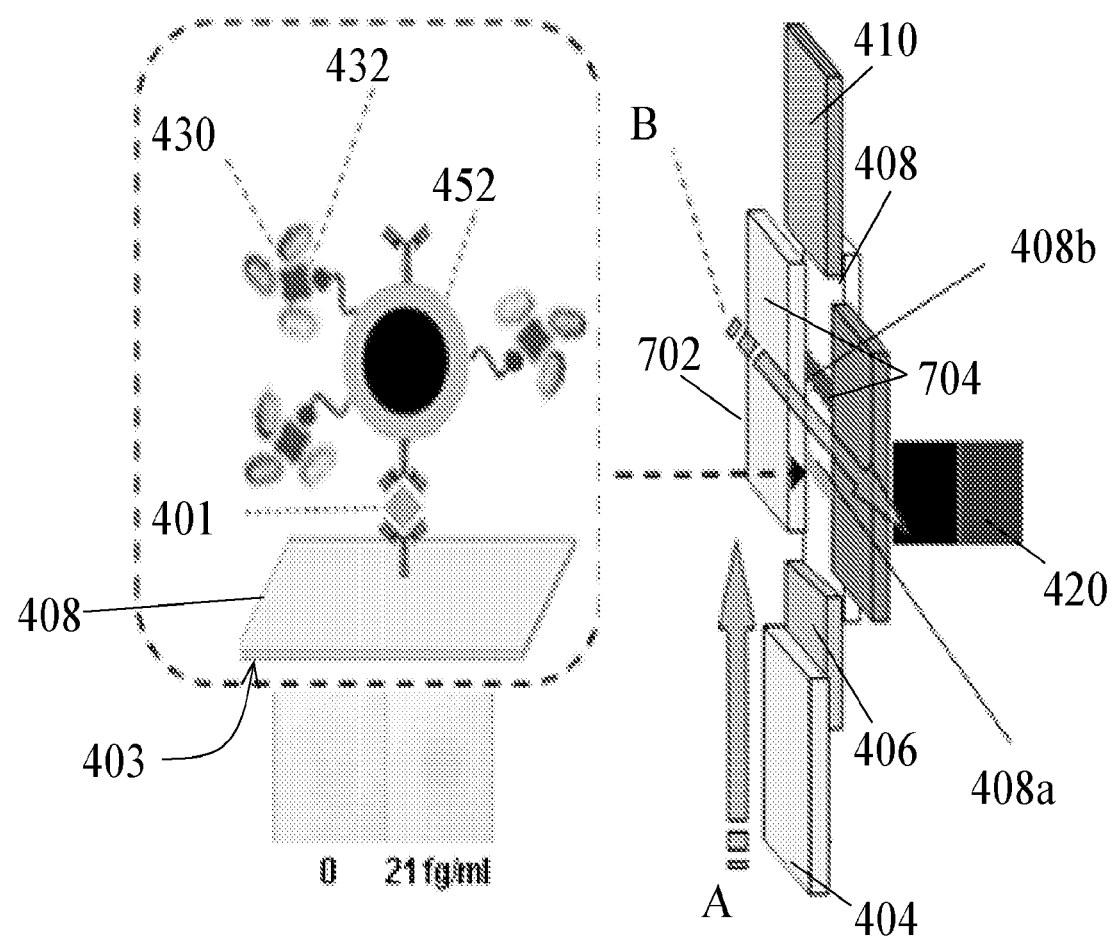
FIG. 7A illustrates the analytical concept of at least one exemplary embodiment of the present inventive diagnostic tool and method, produced by supplying substrate in the cross-flow direction at the site of antigen-antibody (or antigen-aptamer) complex formation while the sample flows in the vertical direction.

As shown in FIG. 7A, the SA-HRP conjugates 430 may be allowed to complex with the target analyte 401 via a biotin linker of a magnetic probe 452 bound to the target analyte 401. Maximizing the number of HRP molecules tethered to the mNP probes 452 facilitates maximum signal enhancement. Two conjugates specially designed for this purpose are a biotinylated gold surface and a streptavidin-HRP construct (i.e. an SA-HRP conjugate 430). First, spatially controlled chemical cross linkers containing biotin are coated onto the surface of mNPs, which are spherical in shape to maximize the surface area. Second, three to four HRP molecules are chemically coupled to streptavidin (SA) by a well-controlled bioconjugation strategy, to improve the degree of labeling of HRP compared to typical SA-HRP conjugates.

Due to the large surface area of mNPs, SA-HRP conjugates 430 can be efficiently bound to biotin via the strong avidin-biotin interaction (molecular affinity is ~$10^{15}$ L/mol) with minimal steric hindrance. Per preliminary experiments, the LOD can be easily enhanced 25-50-fold as compared to the conventional kits with this simple modification alone. By appropriate surface modification of mNPs, optimization of the number and length of spacers may be achieved containing biotin (spacers synthesized by coupling NETS-terminated PEG to biotin-terminated linkers, with PEG endowing strong hydrophobicity to lengthen the spacer). Thus, by improving the degree of labeling with this well controlled conjugation strategy, a 100-fold enhancement of the signal can be achieved. Per supporting experiments, approximately 73 biotin-containing chemical linkers (using HABA assay—Green, 1965) and the number of HRP were around 219 (from SDS-PAGE analysis) on a single 40 nm size gold nanoparticle. Approximately, 3 HRP molecules per SA attached to a biotin linker considering steric hindrance and conjugation efficacy.

Accordingly, as the fluid sample flows through the conjugate area(s) 406, any target analytes 401 present therein—as well as any magnetic probes 452 previously bound therewith—may react and/or bind with the one or more conjugates (thus forming a target analyte-conjugate complex) prior to flowing into the capture area 408. Furthermore, where one of the conjugates comprises HRP, enhanced signal generation can be expected when washed with an appropriate enzyme substrate.

The distal-most conjugate area 406 is in flow contact with the capture area 408 of the mLFIA device 400. As illustrated in FIG. 4B, the capture area 408 is where immunocomplex formation occurs if one or more target analytes 401 are present within the fluid sample. Furthermore, the capture area 408 is where the resulting signals 408a, 408b, 408n are displayed. The capture area 408 may comprise the same material as the other portions of the strip 402 or, in at least one embodiment, may comprise a low-flow membrane strip such as a nitrocellulose membrane.

In any event, the capture area 408 comprises one or more immobilized capture ligands 409 coupled or tethered thereto. Generally, each capture ligand 409 comprises an antibody or an aptamer specific to a target analyte 401. Such immobilized capture ligands 409 'capture' their respective target analyte 401 as the fluid sample migrates by, thus forming an immunocomplex and immobilizing the target analyte 401 (and any conjugate or magnetic probe 452 bound thereto) at an attachment site as shown in FIG. 4B. It will be appreciated that like capture ligands 409 may be concentrated in predetermined locations in the capture area 408 to facilitate generation of a clear signal 408a upon application of an agent that interacts with the HRP conjugate 430 coupled with the target analyte 401. In at least one exemplary embodiment, such an agent comprises an enzymatic substrate such as tetramethyl benzidine (TMB).

Various immobilized capture ligands 409 may be employed in the same capture area 408, which may be especially advantageous when an assay device 100 comprises a multiplex assay configured to simultaneously detect the presence of multiple target analytes 401 in the fluid sample (see the Experiments below for specific examples). For example, a capture area 408 could comprise two (or more) separate groups of immobilized capture ligands 409, with each group comprising an antibody or an aptamer specific to a different target analyte 401. Accordingly, if any of those target analytes 401 are present within the fluid sample, immunocomplexes form between the capture ligands 409 of a group and their respective target analyte 401 such that a signal 408a indicative of the target analyte 401 being present in the fluid sample can be generated at the appropriate attachment sites. FIG. 4A shows an example comprising one attachment site that is specific to a particular target analyte 401 (signal 408a) and one control that captures any particle and thereby shows that reaction conditions are appropriate (signal 408b).

As noted above, the strip 402 may optionally comprise an absorbent area 410 positioned at its end and in flow contact with the capture area 408. Where used, the absorbent area 410 comprises a porous material that simply collects the extra fluid sample that has flown through the strip 402.

The at least one magnet 420 is positioned at or near the capture area 408 of the strip 402. As shown in FIG. 4A, the magnet 420 may be positioned adjacent to a second side of the barrier 403. In operation, the at least one magnet 420 exerts a magnetic force (e.g., an attractive magnetic field) on the target analytes 401 (perhaps more specifically, to the magnetic probes 452 bound thereto) as they move through the capture area 408. In this manner, the magnet 420 controls the movement of the target analytes 401 to focus flow of the same to a specified position or area in the capture area 408.

Benefiting not only from the HRP-amplified signal enhancement, a simple external magnet 420 may be employed to slow down the labelled target analytes 401 as they migrate through the capture area 408 of the strips 402, thereby resulting in prolonged reaction time and increased interaction between the target analytes 401 and the immobilized capture ligands 409. This, in turn, results in capture rates that are significantly increased. As such, the mLFIA device 400 of the present disclosure consistently exhibits a considerably improved LOD over those seen with conventional LFIA devices and methods. Combining the HRP amplification and magnetic field control, the sensitivity of the naked-eye detection scheme can be greatly improved to a near single cell level that has heretofore not been possible.

Integrating LFIA with magnetic focus concepts previously used to separate and enrich bacteria for SERS or fluorescence detection to enable very high detection sensitivity, a LOD nearing a single cell limit can be achieved. Unlike applications that utilize magnetic nanostructures as a preconcentration step or magnetic beacon, the novel strategies hereof control the movement of the target labelled with specific probes to detect 2-3 cells per strip within 30 minutes by the naked eye, while retaining the simplicity of the protocol as a POC analytical method. Furthermore, by incorporating a magnetic preconcentration step, detection can also be performed in complex matrices with further improved sensitivity.

The cost of the novel tools, systems, and methods hereof are comparable to the less effective lateral flow systems currently available. However, significantly, the inventive devices, systems, and methods hereof exhibit clinical sensitivity of greater than about ninety percent (>90%). Furthermore, it has been found that the overall procedure, including an antigen-antibody reaction and the signal generation step, can be completed in less than 30 minutes.

Figure 4C:
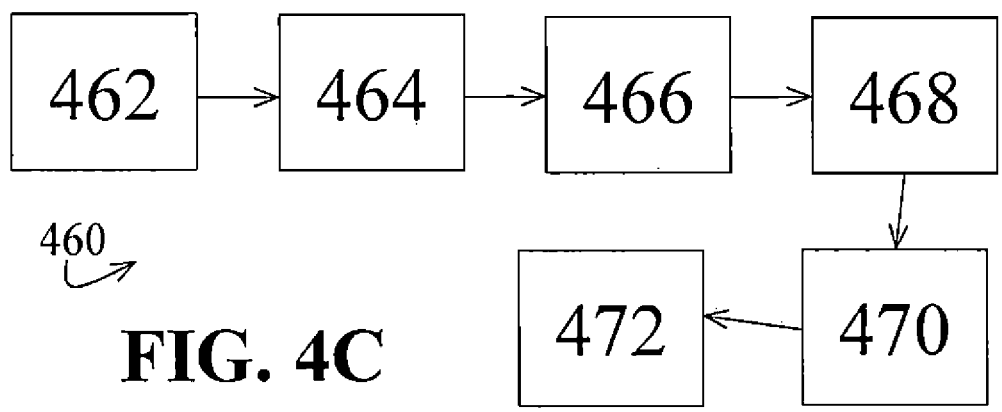
FIG. 4C shows a flow chart representative of a method of detecting one or more target analytes using the assay devices of the present disclosure.
Figure 4D:
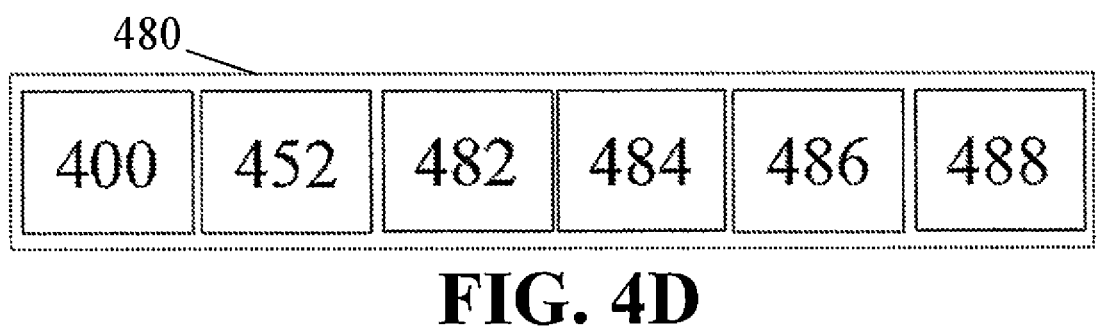
FIG. 4D shows a block representation of a sampling kit according to an exemplary embodiment of the present disclosure.

In another exemplary aspect of the present disclosure shown in FIG. 4D, an exemplary kit 480 is provided that comprises the mLFIA device 400 and various other items necessary or convenient for the POC or other use thereof. For example, in at least one embodiment, the kit 480 is a sampling kit comprising the mLFIA device 400 (with or without supply areas 702 for cross-flow applications), a plurality of magnetic probes 452 for labeling one or more desired target analytes 401, and an agent 482 for signal generation upon contact with a site of immunocomplex formation. Additional items the kit may include are (without limitation) a swab 484 for collecting a tissue or food matter sample from a subject, a container 486 for suspending the tissue or food matter sample in a liquid, and/or an amount of distilled water 488.

In general application, the mLFIA device 400 may be used to identify if one or more target analytes 401 are present within a fluid sample pursuant to the following steps of method 460 (see FIG. 4C). In at least one embodiment, the magnetic probe 452 is added to a fluid sample to be tested such that the probe 452 can bind any target analyte 401 present therein at step 462. It will be noted, however, that the magnetic probe 452 may additionally or alternatively be stored within the conjugate area(s) 406 of the strip 402 and, as such, step 462 may be optional and performed only as needed.

At step 464, the fluid sample is received on the strip 402 of the mLFIA device 400 and allowed to flow in a first direction along the strip 402 for immunocomplex formation in the capture area 408. Where the strip comprises a sample receiving area 404, the fluid sample can be received there; otherwise, the fluid sample may be received in a conjugate area 406 to initiate flow/migration through the strip 402.

In the one or more conjugate areas 406, at step 466, one or more conjugates are tethered to a target analyte 401 present within the fluid sample. As previously described, a conjugate may be specific to a target analyte 401 (e.g., where a conjugate comprises an antibody or aptamer specific to the target analyte 401) or a conjugate may be configured to bind with a magnetic probe 452 coupled with the target analyte 401 (e.g., in the case of SA-HRP). Coupling of the conjugate with the target analyte 401 (either directly or by way of the magnetic probe 452) results in a target analyte-conjugate complex (the "target analyte complex").

At step 468, the movement of the target analyte 401 within the capture area 408 is manipulated through use of a magnetic field generated between the at least one magnet 420 and the magnetic probe 452 of the target analyte complex. In at least one embodiment of step 468, an attractive magnetic field is employed to focus flow of the target analyte complex to a specified position or area in the capture area 408. Indeed, in at least one embodiment, the flow of the target analyte complex may be reduced by the magnetic field to facilitate an increased/optimized reaction time between the target analyte complex and the immobilized capture ligands 409 of the capture area 408.

One or more signals 408*a*, 408*b* are generated at step 470. Signals may appear at both attachment site(s) associated with immobilized capture ligands 409 bound with a target analyte complex, and control bands. In at least one exemplary embodiment, step 470 comprises washing the strip 402 (or at least the capture area 408 thereof) with an agent to facilitate signal generation. Such an agent may comprise an enzymatic substrate and, in at least one embodiment where one of the conjugates comprises SA-HRP, step 470 comprises washing with an enzymatic substrate configured to react with the SA-HRP conjugate 430 to generate a colorimetric signal (e.g., TMB).

Now referring back to FIG. 7A, in at least one alternative embodiment, such inventive devices, systems, and processes may further comprise a two-step cross-flow reaction (vertical and horizontal flow directions, for example) and comprise a reaction time of between about fifteen (15) and about thirty (30) minutes. In this system, the enzyme-catalyzed reaction (a feature distinct from those of other tracers) is conducted separately for enhanced signal generation following the completion of antigen-antibody-binding reactions. As the standard protocols for this type of heterogeneous immunoassays require washing steps for the separation of the immunocomplexes formed on solid surfaces from the unreacted reagents, the method of cross LFIA (cross-LFIA) has been designed where immunological binding and the enzyme-based detection reaction are sequentially conducted in the system in one pass, vertically and laterally.

The concept of cross-LFIA further sensitizes the detection platform described in connection with the mLFIA device 400. In at least one embodiment, the related analytical protocol comprises a two-step process comprising: (i) initiating sample flow through the strip 402 to induce an antigen-antibody (or antigen-aptamer) reaction in the capture area 408, and (ii) initiating the flow of enzyme substrates for colorimetric signal generation.

Primarily, the sample containing the target analyte 401 is absorbed from the bottom of an immunostrip 402 (vertical flow) at the sample receiving area 404 (FIG. 7A) (step 464), inducing an immunocomplex formation at a pre-determined site, on the capture area 408. Second, one or more horizontally arranged supply area 702 are placed on each lateral side of the capture area 408. As with the strip 402, the supply area(s) 702 comprises a porous substrate and is configured for supporting flow of an agent received thereon to the capture area 408. However, while the other areas 404, 406, 408 of the strip 402 support flow in a first flow direction (see arrow A), the supply areas 702 support flow in a second flow direction (see arrow B) that crosses the first. As shown in FIG. 7A, the first flow direction comprises a vertical flow, while the second flow direction comprises a horizontal flow.

The agent received on the supply areas 702 may comprise an enzymatic substrate an enzymatic substrate configured to react with the SA-HRP conjugate 430 to generate a colorimetric signal (e.g., TMB) (e.g., at step 470 of the method 460). Accordingly, in this embodiment, the substrate is added onto the supply pad 702 to initiate enzymatic signal generation (horizontal flow) in an independent step. At the sites of immunocomplex formation, colorimetric signals can be produced by supplying enzyme substrates at the time of signal generation almost instantaneously, a critical advantage of the cross-flow system. In conventional lateral flow assays, the interaction between probe labeled targets and capture antibodies at the signal generation site is governed by capillary action and results in a low capture ratio; however, with the mLFIA concept described herein, by placing a magnet 420 at the capture area 408, the LOD was increased by about 1000-fold.

Furthermore, it is intrinsically possible to measure colorimetric signals of the membrane that are used as a solid support of the system to determine the quantity of the target analyte 401 in the sample. As exemplified in ELISA, enzymes can be used as alternative types of tracers, which can be applied to immunosensors for LFIA. An enzyme tracer can generate a signal resulting from its relatively fast catalytic reaction to provide different types of signals measurable with comparatively simple detectors (e.g., based on colorimetry, chemiluminometry, or electrochemistry) depending on the substrate as well as the enzyme used. Further, signal enhancement is also possible in addition to quantification. By using image processing algorithms specifically designed for a particular test type and medium, the signal intensities obtained from the assay can then be correlated with analyte concentrations. As such, in at least one embodiment, the method 460 may further comprise a signal quantifying step 472. In at least one embodiment, step 470 comprises capturing an image of the colorimetric signal produced on the capture area 408 and analyzing the image to identify a coloration value and/or a light intensity value of the colorimetric signal to determine the quantity of the target analyte 401 present within the fluid sample.

Figure 7B:
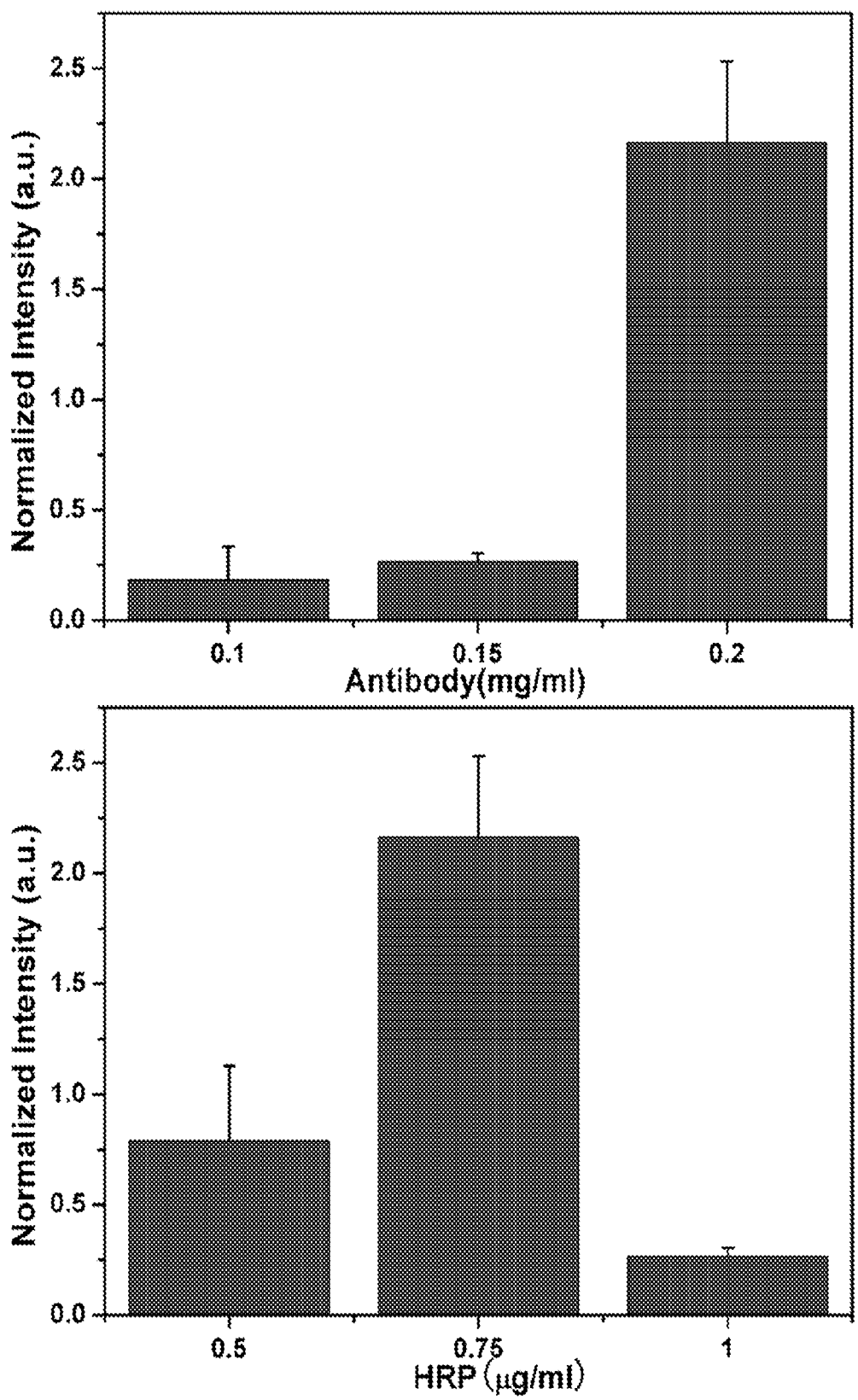
FIG. 7B shows graphs depicting the performance of the inventive magnetic focus concept utilized by the devices and systems of the present disclosure.

In operation, it was determined that VCP at a limit of 16 pg/ml of tissues extracts can be detected using the presently disclosed mLFIA device 400. The current technology optimizes the amount of antibodies at the capture area 408 and the HRP (FIG. 7B) tethered to the nanoparticles to achieve an unprecedented LOD of ~20 fg/ml of purified VCP by colorimetry as shown in FIG. 7B by the spot on the nitrocellulose membrane. As shown in FIG. 7B, the detection performance of the inventive magnetic focus concept utilized by the mLFIA device 400 described herein was investigated with different amounts of antibody conjugated to the LFIA strips 402 and the enzyme, HRP, used in the signal generation step (step 470). It can be seen that the increased number of antibodies in the capture area 408 resulted in an improved signal.

It will be appreciated that there are numerous applications in which the devices, systems, and methods hereof may be employed. For example, and without limitation, two such applications are cancer screening and pathogen detection.

Detection of Food Pathogens

The present devices, systems, and methods can be used to detect foodborne pathogens or other microorganisms, even where such pathogens or microorganisms are only present in small concentrations or amounts. Because food safety standards are rigorous and require stringent protocols and monitoring standards, it would be extremely beneficial to have an easy to use, accurate, and low-cost sampling device and/or system through which a food could be tested for pathogens. The requirements on sensor specifications are also rigorous with the need to be highly sensitive, down to single cell, specific, rapid, and simple with the potential for on-site detection, all of which can be achieved through the ultra-sensitive and specific devices, systems, and methods provided herein. The devices, systems, and methods of the present disclosure can also be applied to patients directly; indeed, they can also be beneficially employed to test a patient (e.g., using a sample of such patient's blood, urine, cells, or other testing medium) for the presence of pathogens or other microorganisms.

In support of these aims and to verify both analytical sensitivity and usability of the device 400, the mLFIA device 400 and method 460 were employed in the rapid detection of *Listeria monocytogenes* (a common foodborne pathogen) in complex matrices. Indeed, the assay device's 400 sensor capabilities and LOD was initially demonstrated in pathogen detection and, similarly, the application can range from protein detection to whole cell monitoring (e.g., pathogen detection). Results of the chromatographic analysis yielded a LOD of 95 and 97±19.5 CFU/mL in buffer solution and complex matrices. In addition to high sensitivity, unlike other typical bacteria detection methods, it was possible to shorten the separation time of bacteria in a given food matrix and complete the detection in less than 30 minutes using the device 400. Furthermore, by employing the integrated concept of using enzyme amplification and gold-based magnetic probes 452 of the present disclosure, it was possible to further extended the LOD for pathogen detection to an unprecedented ~25 cells/ml by magnetic focusing—the lowest LOD achieved to-date using lateral flow based technology on colorimetry for a visual readout.

Accordingly, application of the mLFIA device 400, and methods 460 for using the same, have, vast and promising applications for the rapid detection of pathogens in food products as well as patients themselves. Furthermore, when applied to the detection of food pathogens in a fluid sample, if performance of the method 460 generates a signal indicative of the subject experiencing or suffering from a pathogen, in at least one embodiment, the method 460 may further comprise administering a therapeutic treatment to the subject such as, for example, applying a pesticide or fungicide where the subject comprises food matter or administering a therapeutically effective dose of an antibiotic or other pharmaceutical where the subject comprises a patient.

Cervical Cancer Screening

In at least one embodiment of the present disclosure, a simple point-of-care (POC) colorimetric testing device (configured in accordance with mLFIA device 400) is provided for on-site cervical cancer screening and treatment. The application of such a device is far reaching; indeed, it may be employed for effective POC testing for cervical cancer screening or the like. The testing device is based on the concepts that the transformation and changes a normal cell undergoes to become precancerous and/or malignant has many consequences associated therewith in the expression level and/or function of host genes. As such, detection of these changes (using host biomarkers, for example) improves objectivity, and therefore the reproducibility and reliability of cervical screening, and enables the prediction of clinical outcome by identifying women at high risk for cancer progression. In at least one exemplary embodiment, two or more of these markers are used to increase the sensitivity and specificity of identifying which lesion has potential to progress.

Accordingly, the novel testing devices, systems, and methods hereof are a simple, user-friendly, POC based on four key protein biomarkers that are sensitive and specific in detecting cervical cancer and its precursor lesions (i.e. CIN2/3+). Such targeted markers have been identified using extensive proteomics and other markers that are sensitive and specific for cervical cancer diagnosis, and include (without limitation) the tumor suppressor Valosin-containing protein (VCP)); minichromosome maintenance proteins (MCM2) and topoisomerase (TOP2A)), which are required for DNA replication; and the cell-cycle control protein (p16$^{INK4}$). Additionally, E6 and E7 Human Papillomavirus oncoproteins may also be used as targeted biomarkers.

Several advantages are associated with these protein markers, including that are that they are HPV type- and age-independent and specific for real neoplastic disease (versus viral infection or benign mimickers). As an example of the potential efficacy of the inventive technology set forth herein, VCP was detected at an unprecedented LOD (about fg/ml) in between about 15 to about 30 minutes. The inventive tools, systems, and methods hereof can also detect p16$^{INK4}$, MCM2, TOP2, E6, and E7 proteins with equivalent sensitivity. To aid in understanding of the inventive concepts set forth herein, a brief discussion of the biomarkers of interest is now provided, followed by a more detailed review of the inventive tools, systems and methods of the present disclosure as they apply to cervical cancer screening applications.

Targeted Markers

Figure 5A:
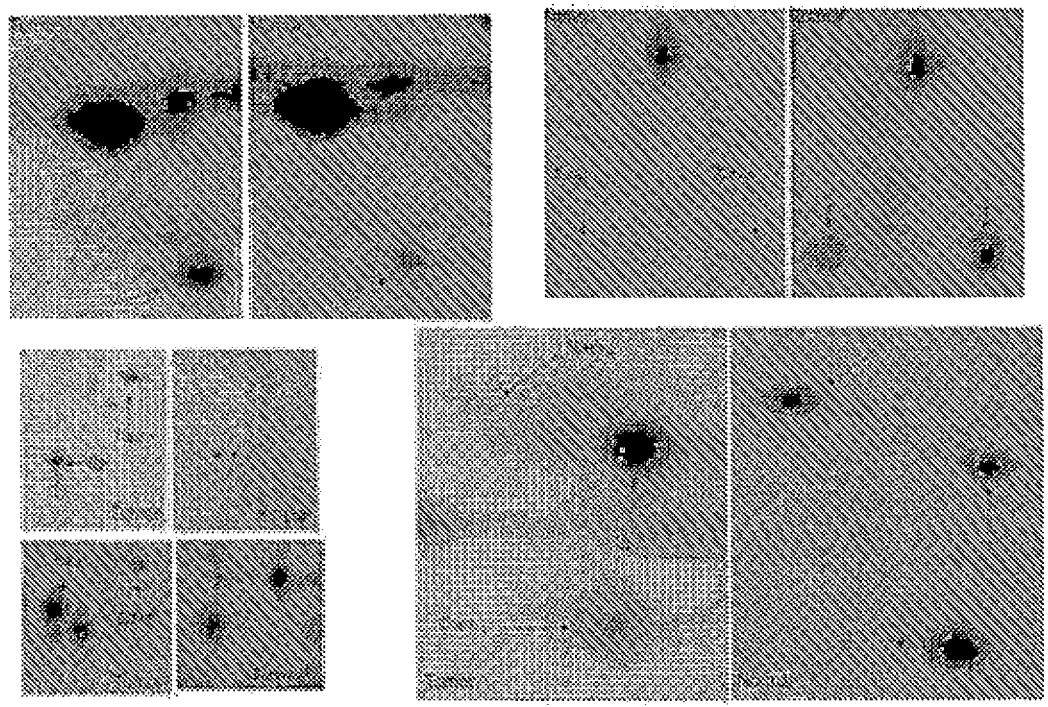
FIG. 5A shows electrophoresis gels with differentially expressed proteins in cervical carcinoma (cc) as compared to normal adjacent tissues.
Figure 5B:
FIG. 5B shows results of a Western blot validation of VCP protein detected by proteomic studies in the normal adjacent (N) and cervical carcinoma tissues (c); B-actin loading control is shown in the lower panel (N denotes normal tissues (1N, 2N, 3N), T denotes tumor tissues (2T, 3T, 4T, 5T) and precancerous tissues (6T and 7T)
Figure 5C:
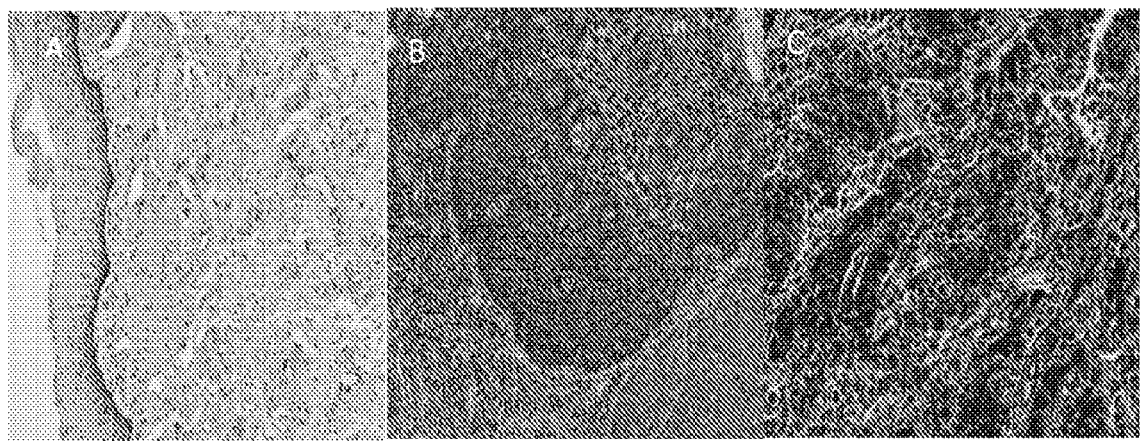
FIG. 5C shows IHC staining results of normal (A), CINIII (B), and cancerous cervical tissues for VCP protein; no staining is observed for VCP in the normal tissues (A), intense staining was observed in the cytoplasm of CINIII (B), and tumor cells (C)

Valosin-Containing Protein. As mentioned above, embodiments of the tools, systems, and methods of the present disclosure identified VCP at 20 fg/ml. VCP was identified as a result of proteomic study of invasive and preinvasive cervical lesions (CIN2/CIN3) and normal cervical tissue (FIG. 5). The objective was to identify sensitive and specific markers for the early detection of cervical cancer. Upon completing the proteomic study, VCP was identified to be highly expressed in high-grade preinvasive and invasive cervical cancer lesions, which was confirmed using Western blot (FIG. 5B) and immunohistochemistry (FIG. 5C) in another set of cervical tissue samples (n=200; normal, CIN1, CIN2, CIN3, and carcinoma) either obtained from Indiana University School of Medicine tissue bank or purchased from US BioMax, Inc. (Rockville, Md.). VCP identified CIN2, CIN3, and carcinoma (invasive cancer) with high sensitivity (93%) and specificity (88%).

VCP is essential for cell cycle progression in all phases of the cell cycle and is an abundant AAA-ATPase associated with many essential cellular functions. VCP is known to be involved in the ubiquitin/proteasome degradation pathway, which works in both up-regulation of cell proliferation and down-regulation of cell death in human cancer cells. Evidence from analyses of large patient cohorts demonstrated that significant increases in expression of VCP in tumor cells often correlate with disease progression. Furthermore, VCP over-expression was found to be linked directly to HR-HPV mediated activation of protein tyrosine phosphatases, non-receptor type (PTPNs), which are believed to exert oncogenic functions.

Cyclin-dependent kinase inhibitor 2A (P16INK4a). The second marker chosen in the panel is the $p16^{INK4a}$, which is a surrogate marker of cell transformation. $p16^{INK4a}$ is a tumor-suppressor protein (a cyclin-dependent kinase inhibitor) that is overexpressed in atypical dysplasia and carcinoma of the cervix. $p16^{INK4a}$ inhibits cell proliferation by deactivating the cyclin-dependent kinases that phosphorylate retinoblastoma protein (pRb). Binding of Rb to E2F blocks E2F-driven cell-cycle activation and entry into S-phase of the cell cycle. In the case of transforming HPV infection, E7 viral oncoprotein prevents binding of Rb to E2F transcription factor, causing increased levels of P16INK4a, the detection of which may signify persistent HPV infection. Recently, $p16^{INK4a}$ has been accepted as a sensitive and specific marker of dysplastic cells of the cervix and is a useful biomarker for cervical cancer lesions diagnosis and cervical screening. A diagnostic test, CINtec Plus, by MTM laboratories AG (Heidelberg, Germany) has been formulated using an immunohistochemistry-based $p16^{INK4a}$ and Ki-67 antibody cocktail. In Europe, for the European Equivocal or Mildly Abnormal Pap Cytology Study (EE-MAPS), the sensitivity of the CINtec test for biopsy-confirmed CIN2+ was 92% for atypical cells of undetermined significance cases and 94% for low-grade squamous intra-epithelial lesions, with specificity of 81% and 68%, respectively. In addition, a $p16^{INK4a}$ ELISA assay detected CIN3 with an estimated sensitivity in the range of 80-95%, which is comparable to the HPV DNA test (Hybrid Capture 2). However, the $p16^{INK4a}$ ELISA test was more specific compared to the Hybrid Capture 2 test, resulting in fewer false-positive test results. However, the test is designed to either complement cytology or be ELISA-based and, thus, cannot be performed at the point of care. There are also infrastructure requirements for tissue fixation, paraffin embedding and sectioning as well as a requirement for continuous supply of antibodies and staining reagents. Additionally, the test can only be performed by trained laboratory personnel who are required for immunostaining and the results must be interpreted by a pathologist.

Minichromosome maintenance protein 2 (MCM2). The third protein biomarker considered in the CERVBIO panel is MCM2, a cell-cycle regulatory protein that is important for DNA replication and formation of pre-replicative complexes during the G1 cell-cycle phase. Its overexpression is linked to HPV infection through the E2F transcription factor pathway. Overexpression of this protein can be detected immunohistochemically in high-grade cervical lesions. MCM2 together with topoisomerase (TOP2A) (the fourth protein included in the CERVBIO panel described herein) formulated into a cervical cancer screening kit, ProExTMC, commercially available and marketed by Becton Dickinson.

Topoisomerase (TOP2A). TOP2A is an enzyme that plays an important role in DNA replication by affecting the topological structure of the DNA through interaction with the double helix. ProExTMC, MCM2 and TOP2A have each been reported to detect cervical disease with a higher level of specificity and positive predictive value than current methods of HPV detection or cytology-based diagnosis. A limited number of clinical studies have shown that Pro-ExTMC has a sensitivity ranging between about 0.67 and about 0.99 and specificity ranging between about 0.61 and about 0.85. However, despite ProExTMC's high sensitivity, the test cannot be performed at the POC. Similar to the commercially available P16INK4a and Ki-67 test, CINtec, the ProExTMC test requires sophisticated laboratory environments for immunohistochemistry. FIG. 6 shows the sensitivity and specificity, protocol and disadvantage of commercially available tests to detect the three proteins compared to the APTIMA HPV test and other HPV DNA tests.

As previously discussed, there is a worldwide need for a simple to use, cost effective, and accurate point-of-care tool for cervical cancer screening in particular. When combined with the enhanced LOD provided by the inventive devices, systems, and methods of the present disclosure, the biomarkers described herein not only improve the current diagnosis and staging of cervical cancer, but are also paramount for early detection because the biomarkers and/or proteins can be detected even when present in small amounts. This is extremely significant because conventional systems and methods cannot detect such low levels or concentrations of analytes as are typically seen with such diseases and/or disease risk factors, nor can conventional systems/methods accurately and dependably detect molecules that are smaller than pathogens. Finally, the technology does not require any intricate steps or operation and, thus, is readily applicable to low resource settings.

Having demonstrated the application of the magnetic focus enhanced lateral flow (mLFIA) concept in infectious pathogen detection, the current disclosure will now describe specifics of the assay device's 400 potential as a POC for cervical cancer biomarker detection. To achieve both high sensitivity accompanied by the detection of multiple targets, embodiments of the present disclosure use a LFIA concept employing gold-based magnetic nanoparticles (mNPs) in combination with enzyme (horseradish peroxidase; HRP, for example) used as a tracer. It has been found that the overall method 460, including an antigen-antibody reaction and the signal generation step 470, can be completed in less than 30 minutes.

At the same time, the best signal was not obtained for a high concentration of HRP. According to the optimization shown in FIG. 7B, optimization of antibody number and HRP amount can improve the signal around 10-fold, resulting in better detection sensitivity. By comparison, the currently described approach exhibits at least a $10^2$-$10^4$ fold enhanced LOD compared to conventional LFIA kits in the market due to the enhancement from HRP enzyme labels and increasing the interaction time with our recently developed magnetic focus concept for POC detection.

Figure 8:
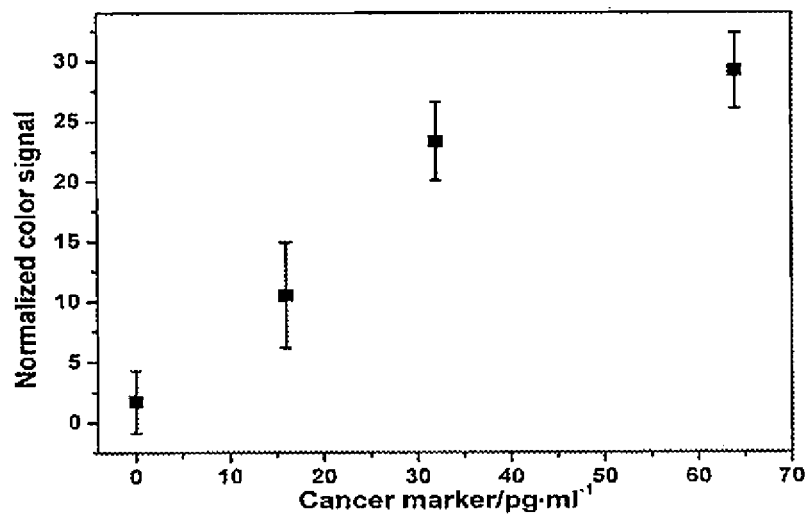
FIG. 8 shows a graph depicting the results of VCP detection in tissue extracts with the proposed mLFIA.

FIG. 8 shows a calibration plot of the VCP levels in serial concentrations of tissue extracts detected by at least one exemplary embodiment of the magnetic-focus LFIA (mL-FIA) method 460 hereof. The clinical sensitivity is >90% with an unparalleled LOD. In testing the novel approach described herein, antibodies as well as aptamers were used, the specificity of which were tested and compared with that of antibodies. Quantification was achieved by integrating the readers already developed by Chembio Diagnostic Systems Inc. (CDS). The biomarkers used were based on preliminary and recent data and other markers (P16INK4a, MCM2, TOP2). Compared to commercially available cervical screening tests, the disclosed POC technology can be readily implemented in low resource settings.

In sum, to achieve high clinical sensitivity and specificity accompanied by the detection of multiple targets, a simple, rapid, and highly sensitive LFIA concept was incorporated, employing nanoparticles in combination with enzyme enhancement (e.g., HRP) and a magnetic field to allow for a focused interaction of the capture reagents and the target compared to the conventional capillary flow that occur in all LFIA systems. As previously noted, in this system the enzyme reaction (a feature distinct from those of other tracers) was conducted separately for enhanced signal generation following the completion of antigen-antibody-binding reactions, where the interaction time at the signal generation site/capture area can be improved with a magnetic field provided by a simple magnet to increase the LOD to the pg/ml level and to fg/ml. Since conventional protocols for this type of heterogeneous immunoassay require washing steps for the separation of the immune complexes formed on solid surfaces from the unreacted reagents, the method of cross LFIA was integrated, where immunological binding and the enzyme-based detection reaction are sequentially conducted in the system in one pass, vertically and laterally without any rotation or movement of the lateral flow strip for POC testing in remote settings. Accordingly, the target in the sample first interacts with the gold-based magnetic nanoparticle(mNPs) probes which, in turn, interacts with the capturing ligands at the signal generation site/capture area to produce an enhanced signal upon substrate (TMB: tetramethyl Benzidine) application (line 408*a* in FIG. 7A; line 408*b* denotes control), resulting in the detection of VCP at ~20 fg/ml. Furthermore, if performance of the method 460 generates a signal indicative of the subject experiencing or being at risk for cervical cancer or an infection of the cervix, in at least one embodiment, the method 460 may further comprise performing follow-up treatment and/or administering a therapeutic treatment to the subject such as, for example, administering a therapeutically effective dose of a pharmaceutical or other therapy.

EXAMPLE 1

Cervical Cancer Screening with Multiple Targets

Procedure:
Capturing Ligands. Antibodies and Aptamers: (i) Antibodies for the four markers were commercially obtained from Abcam (VCP: Anti-VCP antibody Cat# ab11433, p16INK4a. Anti-p16INK4a antibody Cat # ab54210, MCM2: Anti-MCM2 antibody Cat# ab108935, and TOP2A: Anti-Topoisomerase II alpha antibody Cat# ab52934). In parallel, aptamers specific to the four proteins of interest were fabricated by Base Pair Biotechnologies Inc.
Steps Involved in Detection are Detailed Below:
Step a: a cotton swab was used to collect the samples from patients; however, samples may be collected in any manner known in the art. Specimen was obtained by rotating the swab several times until the swab is completely saturated with the specimen. The swab is placed in the extraction tube with buffer reagent solution and shaken/rotated, so that the specimen is completely suspended in the solution. After this extraction step, the sample solution is applied to the mLFIA system (mLFIA device 400) (taking about 3 to about 5 min to complete this step (step 464 of method 460)). Optionally, the sample extraction and detection step may then be optimized to achieve a limit of detection of 100 pg/ml as a first step of optimization. Thereafter, the reagents will be further improved to detect sub 20 pg/ml LOD.

Step b: upon placement of the sample in the sample receiving area 404, the sample migrates upward along the immunostrip 402 (vertical flow) and the target-aptamer (or target-antibody) reactions are allowed to occur at the next step (step 466) where biotin linker bearing mNPs with primary antibodies and SA-HRP conjugates are allowed to complex with the target 401 (see FIG. 7A). The target analyte 401 released from the specimen with the bio-active complex is captured by the corresponding capture antibody 409 immobilized at a pre-determined site of the nitrocellulose membrane (this step can be completed in less than about 10 min). Using a simple magnet, the duration of interaction of the mNP conjugate at the signal generation site can be increased (step 468), to result in exquisite sensitivity (~16 pg/ml) as demonstrated in preliminary studies, which can be optimized to reach fg/ml levels by visual detection (FIGS. 7A and 7B).

Step c: for color signal generation, two horizontally arranged supply areas 702 are placed on each lateral side of the signal generation pad/capture area 408 and an enzyme substrate solution containing tetramethyl benzidine (TMB) is then added onto the supply area 702 (step 470). This solution flows across the signal pad/capture area 408 (horizontal flow), to initiate the production of a colorimetric signal 408*a* from the enzyme 430 contained in the immunocomplexes formed at the respective sites (color signals can be generated in 3 min). In at least one exemplary embodiment, prior to this Step c, one or more optional washing steps may be performed. In such embodiments, the signal generation pads/capture areas 408 may be washed with water (or other appropriate substance) to remove any unbound probes 452.

Figure 9:
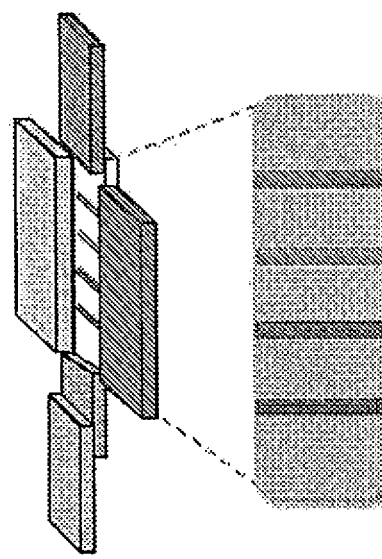
FIG. 9 illustrates a multiplex detection of cervical cancer biomarkers based on cross-LFIA; each binder (antibody or aptamer) that is immobilized can capture the corresponding specific analyte with high affinity and specificity.

Step d: for multiple detection of cancer markers using the mLFIA platform/mLFIA device 400 (see FIG. 9 illustrating at least one embodiment of a multi-marker capture area 408), monoclonal antibodies with high affinity or specifically designed aptamers may be used. In at least one embodiment of the method 460 disclosed herein, this immunoreaction step is critical and may be carefully designed to avoid a decrease in binding affinity as well as cross-reactivity among the binders. By means of the lateral-flow assay as noted above, each target marker 401 can be captured by the corresponding capture ligand 409 (antibody or aptamer) that is immobilized at a pre-determined site on the nitrocellulose membrane, which further enables the formation of a sandwich complex with the detection of capture ligand-labeled with the enzyme-mNPs conjugate as described above. As is known in the art, the signal associated with each pre-determined site/immobilized immunocomplex formation may be color coded or otherwise visually distinguishable from the other signals.

Quantification:
After the analytical procedure and tests for sensitivity and specificity are established, the next step is the quantification procedure (step 472). The color signals that appear on the nitrocellulose membrane (i.e. capture area 408) of the immunostrip 402 can be captured as images using a mobile device with a camera and mobile application (e.g., a smart-phone or tablet device running an application on a microprocessor or otherwise) or a reader (i.e. a cheap digital camera installed within the colorimetric detector running an application on a microprocessor or otherwise) (estimated total cost of the reader with the camera will be less than about $400 USD).

Once an image of the color signals on the immunostrip 402 is taken, in at least one embodiment, the application recognizes an area of the image that is supposed to exhibit colorations (from nanoparticles or products catalyzed by enzymes) and light intensities of red, green and blue channels are collected for that area. In at least one embodiment, the underlying application will remove any saturated or background noise data (via digital filtering or as otherwise known in the art). Initially, auto-exposure and auto-focusing modes may be utilized, while—in certain embodiments—such exposure and focusing are locked for subsequent assays such that the lighting conditions can be maintained the same for a specific set of assays. Alternatively, a feedback algorithm may be incorporated into the application to adjust the light exposure into an optimum window (e.g., 50-200 out of 255=8 bit). In at least one embodiment, green (for product catalyzed by enzymes) or red absorbance (for gold nano-shells) are recorded using the absorbance definition $A=-\log(I/I0)$. I0 can be measured by recording green channel intensities on the background paper (where antibodies are not loaded).

Figure 10:
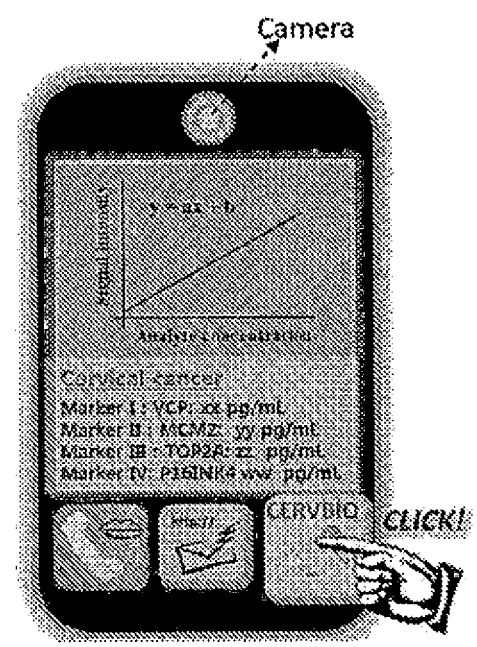
FIG. 10 shows at least one embodiment of a screenshot of a cervical cancer quantification cell phone app pursuant to at least one exemplary embodiment of the present disclosure.

With the mobile device concept (FIG. 10), appropriate media software, hardware, and applications may be employed with the respective calibration standards and peak and curve analysis programs which are easily programmed and updated. Alternatively, a user can be prompted to construct a standard curve using a series of positive control solutions. In certain embodiments, the mobile-device-based assay may be optimized to further improve the sensitivity by tilting the smartphone at a certain optimized angle to minimize the background Mie scatter. Alternatively, with the reader concept, the camera may be mounted on the ceiling of the chamber, and light-emitting diode also installed to automatically illuminate when the immunostrip 402 is inserted. The obtained signals will be subsequently digitized to optical densities in the vertical direction of the immunostrip 402 using appropriate software with inbuilt calibration standards for readout.

Potential Clinical Utility:

As mentioned above, cytology-based cervical screening testing is not affordable or practical in LMICs. On the other hand, VIA has only moderate sensitivity (62-80%) and specificity (77-84%) for detection of high-grade CIN; while HPV tests have high sensitivity, the test suffers from low specificity. The devices, systems, and methods described herein can address the limitations of conventional tests by providing high sensitivity (~95%) and specificity (~90%). Furthermore, embodiments of the inventive assay disclosed herein have the ability to detect four cervical cancer-relevant proteins (VCP, P16IINK4a, M2M, and TOP2A), with VCP having a high sensitivity and specificity for the detection of high-grade cervical lesions, and the proteins p16INK4a, MCM2 and TOP2A having high sensitivity and specificity in detecting high-grade cervical lesions. Combining these four markers results in an increase in the sensitivity and specificity of the inventive assay to ~90%. Accordingly, combining the described signal enhancement strategy with the proposed magnetic focus concept using gold-based magnetic nanoparticles (mLFIA device 400 and related method 460), the results hereof evidence that purified cervical protein VCP can be detected at a limit of 21 fg/ml in PBS (16 pg/ml tissue extract) using the inventive lateral flow concepts hereof (integrating the magnetic focus with enzyme enhancement). The LOD can also be further enhanced by optimizing the procedure, by optimizing the number of enzymes 430 participating in signal generation step (step 470), along with increasing the interaction time between the target protein 401 (present in the sample) and the capture ligand 409 (aptamers or antibodies tethered to the lateral-flow membrane strip at the analyte capture zone) (step 468), to complete the detection within 30 minutes. The demonstrated approach combined with enzyme enhancement in a cross-flow format and the magnetic focus shows tremendous promise to detect the cervical cancer biomarkers that are present at the femtogram level and possibly lower compared to immunohistochemistry, ELISA testing or the lateral-flow platform used in HPV tests.

EXAMPLE 2

Network Formation Approach

Additional embodiments of the present disclosure comprise devices that yield a LOD that is a 1000-fold enhanced over any of the existing platforms due to the use of magnetic focus and signal enhancement. This LOD can be further enhanced using a network formation approach.

Figure 11:
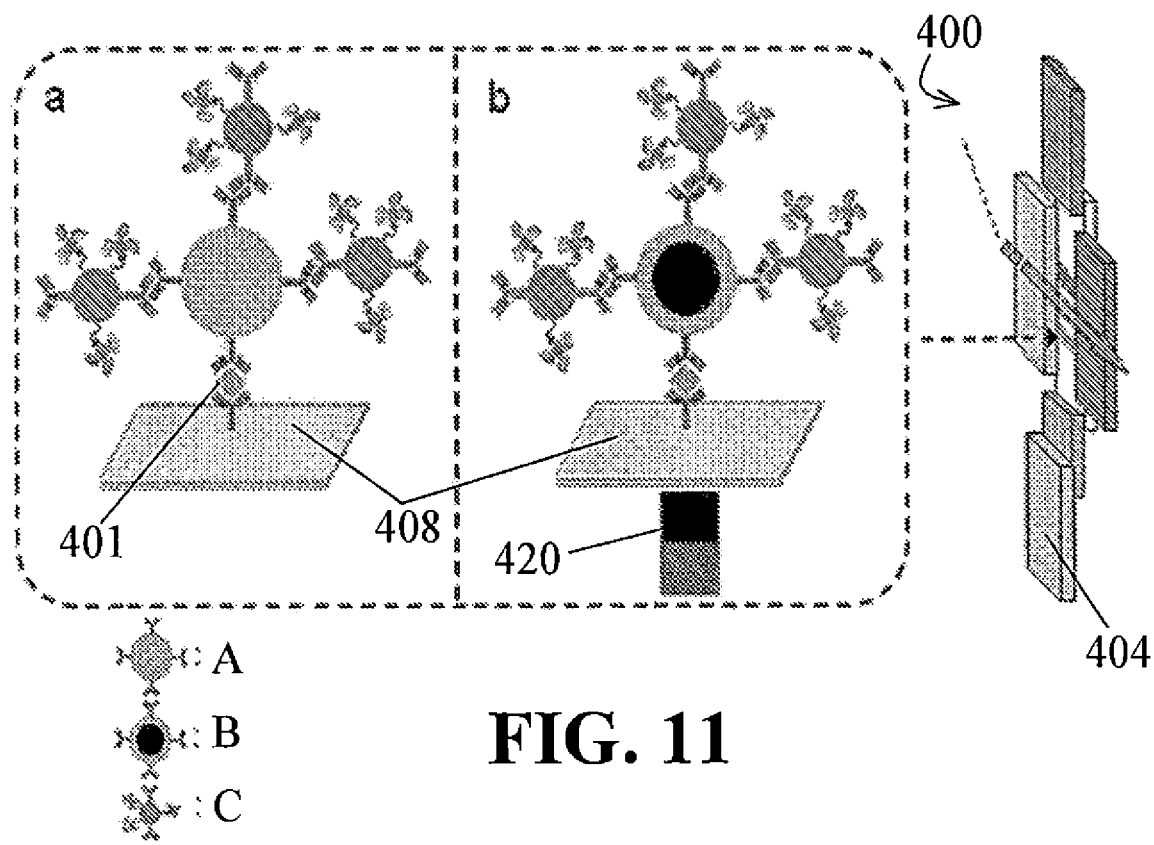
FIG. 11 subpart (a) shows an LFIA with amplified signal enhanced by a network of AuNP probes and subpart (b) shows a magnetic focus LFIA integrated by a AuNP network.
Figure 12:
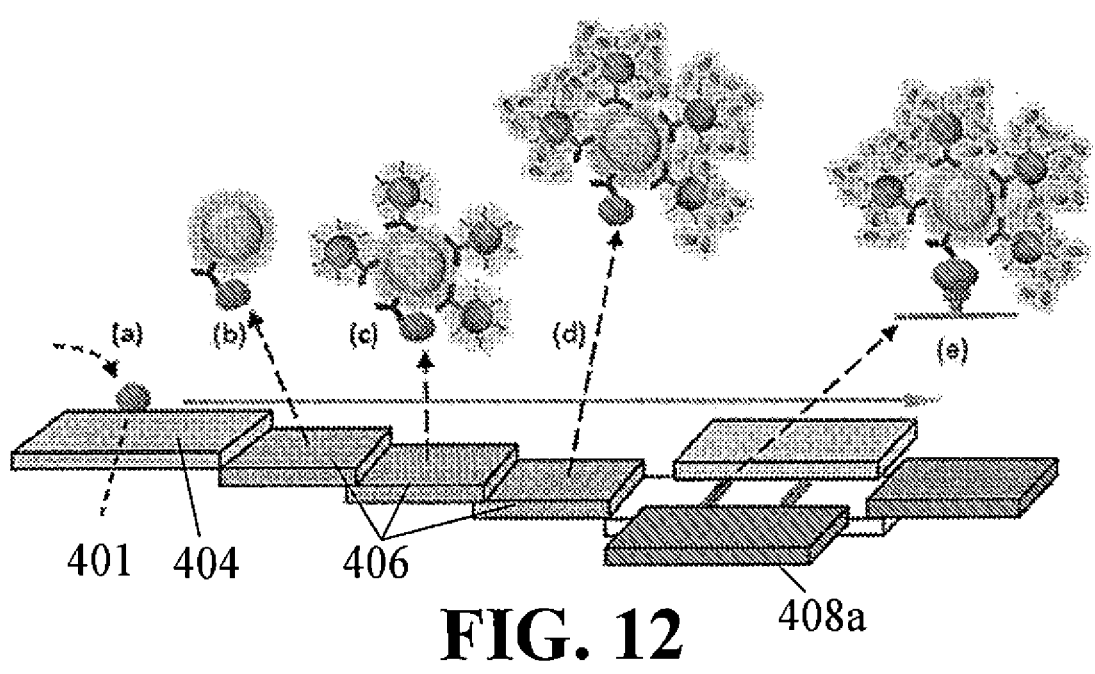
FIG. 12 illustrates a pictorial depiction of at least one embodiment of at least one exemplary method of the present disclosure, showing (a) the target being applied, (b) the target bound to AuNP (40 nm) with first antibody, (c) several biotinylated AuNP (20 nm) conjugates bearing antibodies (secondary) specific to first antibody can be bound to the 40 nm AuNP to form a network, (d) numerous SA-HRP conjugates can then be coupled to the branched biotin on the AuNP with a secondary antibody, and (e) enhanced colorimetric signal.
Figure 13:
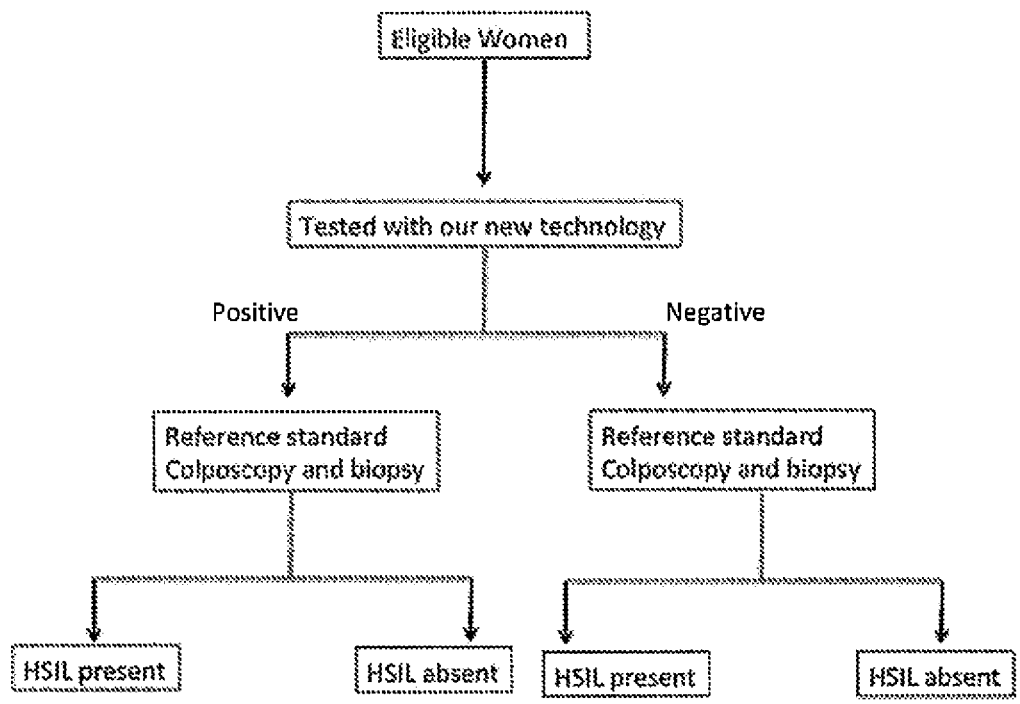
FIG. 13 shows a flow chart of at least one embodiment of a cross-sectional study strategy.

To achieve further enhancement of the signals, two different size AuNP conjugates (e.g., 40 nm (labeled as A in FIGS. 11 and 12) and 20 nm (labeled as C in FIGS. 11 and 12)) may be employed as shown in FIGS. 11, subpart a, and 12. After the target analyte 401 is applied to the sample receiving area 404 (see (a) of FIG. 12), it migrates along the immunostrip 402 in the vertical direction (note, FIG. 12 is rotated for ease of presentation) to sequentially react with the 40 nm AuNPs (A) and the biotinylated second AuNPs (20 nm) (C) bearing the secondary antibodies targeting the primary AuNP (see (b) of FIG. 12). Thereafter, streptavidin (SA)-HRP conjugates 430 that are positioned in the different membrane pads (i.e. one or more conjugate areas 406) are complexed with the 20 nm AuNPs (C) complexed with the 40 nm AuNP (A) to increase the number of HRP enzyme labels to produce a signal 408a that yields greater than 400-fold enhancement, as compared to conventional Lateral Flow Immunochromatography systems. The solution containing these target analyte complexes reach the region of capture probes 409 on the nitrocellulose membrane (i.e. capture area 408), and the complex is then captured by a primary antigen-antibody interaction (see (e) of FIG. 12) to produce a calorimetric signature 408a that is much enhanced. Quantification of the markers 401 may then be performed using a camera within a cell phone (or using other techniques described herein or otherwise known) with an application that contains the calibration and the limits of the different biomarkers or with the readers developed by CDS.

EXAMPLE 3

Evaluation of Clinical Sensitivity and Specificity

Sensitivity is a measure of the proportion of the population that is positive and is correctly identified as such (probability of a positive test given that the patient has the disease). Specificity refers to the proportion of the position that is negative and is correctly identified as disease free (probability of a negative test when the patient is healthy). The analytical performance of the device 400 and related method 460 was evaluated at the UG3 phase using 1000 samples from the tissue bank and 100 samples from Zambia. In the UG3 evaluation, known positive and negative controls were used and, depending upon performance, the controls and calibration samples were increased to increase the power of the test.

As previously discussed, the disclosed testing techniques involved four proteins. For each of these tests, the sensitivity and specificity based on the "known" positive and negative tissue samples from the tissue bank are first evaluated. For prediction of disease status when the true disease status is unknown, the four tests serve as independent predictors in a logistic regression model. For each patient, the point estimate and 95% confidence interval of the odds of having the disease are reported. A simpler alternative to using a logistic regression model is to declare the woman positive for cervical cancer if she tests positive for "at least" one of the protein markers. This method, although simple to use in practice, may have less power compared to using a full logistic regression model; however, it may serve as a useful and quick alternative for a cost-effective preliminary analysis of the samples.

Accordingly, the tools, systems, and methods described herein comprise a multiplex assay with high sensitivity and specificity in identifying high-grade cervical intraepithelial lesions. Cervical cell cycle impairment due to HPV infection or otherwise can be detected with this assay independent of the HPV type and age. The inventive assay will have the ability to detect four proteins (VCP, $p16^{6IINK4a}$, M2M, and TOP2A), with the accuracy of $p16^{INK4a}$ testing having been evaluated in the triage of abnormal cervical samples with atypical squamous cells of undetermined significance (AS-CUS) and low squamous intraepithelial lesions (SIL) cytology either alone or in comparison with HPV DNA Hybrid Capture 2 test. Large meta-analysis including seventeen studies showed that the pooled sensitivity of $p16^{6INK4a}$ to detect CIN2 or worse was 83.2% (95% CI, 76.8%-88.2%) and 83.8% (95% CI, 73.5%-90.6%) in ASCUS and low SIL cytology, respectively, and the pooled specificities were 71% (95% CI, 65%-76.4%) and 65.7% (95% CI, 54.2%-75.6%), respectively. In comparison to the Hybrid Capture 2 test, both tests had similar sensitivity, but $p16^{INK4a}$ had a statistically significant higher specificity in the triage of women with ASCUS (relative sensitivity, 0.95 (95% CI, 0.89-1.01); relative specificity, 1.82 (95% CI, 1.57-2.12)). However, when both test were compared in triaging women with low-grade squamous intraepithelial lesion (LSIL), $p16^{INK4a}$ had significantly lower sensitivity but higher specificity compared with Hybrid Capture 2 (relative sensitivity, 0.87 (95% CI, 0.81-0.94); relative specificity, 2.74 (95% CI, 1.99-3.76). Further, another study showed that overexpression of $p16^{INK4a}$ can predict the development of CIN2 within 3 years among HPV positive women, especially those aged 35-60 years. In addition, more number of CIN2+ was detected in $p16^{INK4a}$-positive women (8.8% (95% CI, 5.8-11.8)) than in negative women (3.7% (95% CI, 1.9-5.4)) and CIN3+ was detected more frequently in $p16^{INK4a}$-positive women (4.4% (95% CI, 2.3-6.6)) than in negative women (1.3% (95% CI, 0.2-2.3)) during follow up. Further, MCM 2 and TOP2A proteins are expressed in cells with aberrant S phases. Elevated expression level of HPV E6 and E7 in transformed cells may also result in overexpression of these proteins. Becton-Dickinson developed a test based on antibody cocktail recognizing these two proteins, called ProEx-CTM assay. The ProExCTM had a higher sensitivity for detecting women with LSIL, but lower specificity to identify cases with high SIL compared to $p1^{6INK4a}$.

The combination of the disclosed cocktail of antibodies/aptamers and the highly enhanced detection platform 400 described herein was consistently found to bind these 4 proteins and provided superior sensitivity and specificity for the detection of cervical cancer high-grade lesions. The unique cross path (dual path or cross-flow) platform 400 of the present disclosure offers an increased analytical, as well as clinical sensitivity, as compared to immunohistochemistry, ELISA testing, and the Lateral Flow platform used in OncoE6 test.

EXAMPLE 4

Verification of Pathogen Screening

In at least one exemplary embodiment of the present disclosure, an LFIA detection platform/mLFIA device 400 comprises the use of magnetic nanostructures modified with antibody as probes 452 to yield an unprecedented LOD for pathogen monitoring by visual readout. Benefiting from not only the HRP-amplified signal enhancement, a simple external magnet 420 is employed to slow down the labelled target pathogens 401 at the detection zone/capture area 408 of the LFIA strips 402, which results in a prolonged reaction time and a stronger signal. Combining the HRP amplification and magnetic field control, the sensitivity of the naked-eye detection scheme was greatly improved to a near single cell level not before possible with conventional technologies. Compared with the conventional methods based on LFIA, the approach of this exemplary embodiment is rapid and simple and requires no pre-enrichment or preculture steps.

Unlike the previous methods based on ITP or a pillar concept based on wax pillar pattern built-in strip to reduce the flow speed, the schemes disclosed herein use only a simple magnet 420 to focus the pathogens 401 labelled with the magnetic nanoparticles 452 modified with target-specific antibodies at the detection zone/capture area 408 more efficiently. Indeed, contrary to conventional applications that utilize magnetic nanostructures as a preconcentration step or magnetic beacon, the disclosed strategy and mLFIA device 400 is the very first effort to utilize magnetic nanostructures 452 to control the movement of the target 401 labelled with specific probes 452 to detect 2-3 cells per strip within 30 min by the naked eye while retaining the simplicity of the protocol as a point-of-care analytical method. Furthermore, by optionally incorporating a magnetic preconcentration step, detection can also be performed in complex matrices to even further improve sensitivity.

Figure 14:
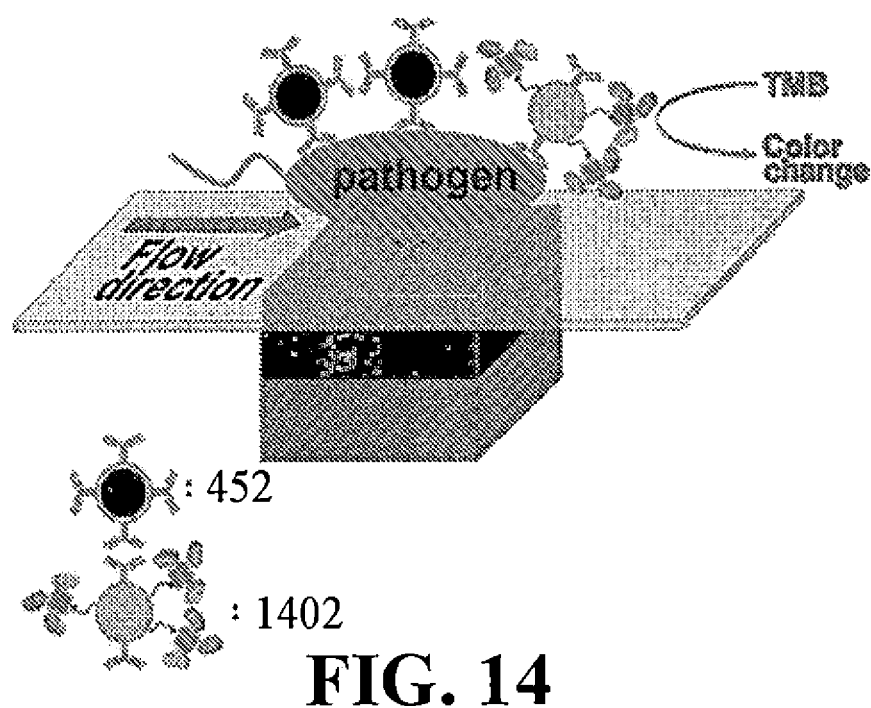
FIG. 14 shows as schematic view of at least one embodiment of a magnetic focus LFIA platform of the present disclosure.

The mLFIA detection of this at least one exemplary embodiment illustrated in FIG. 14. To control the movement and to amplify the color signal, in this embodiment, two different probes were used: (i) magnetic probes 452 comprising $Fe_3O_4$/Au core-shell nanostructures modified with antibodies against specific pathogens 401 to slow down the movement of the captured bacteria with an external magnetic field applied by a simple magnet placed at the detection zone 408; and (ii) AuNP probes 1402 comprising of gold nanoparticles functionalized with antibodies against the same pathogens 401 and biotin to link streptavidin-HRP 430, which reacts with TMB for signal generation for visual detection. For reference, approximately 109 HRP molecules can be attached to a single gold nanoparticle.

In operation, when the bacteria 401 labelled with magnetic probes 452 and AuNP probes pass the detection zone 408, the magnetic field from the magnet 420 positioned below the detection zone 408 slows down the migration of the labelled bacteria 401, thus resulting in a longer interaction time. The increased interaction time improves the amount of labelled bacteria 401 fixed at the detection zone, resulting in a stronger signal. This strategy overcomes the limitation of low surface reaction between bacteria and capture antibody in LFIA. Additionally, the use of two types of probes allowed for the amount of magnetic probes 452 at the detection zone 408 to be optimized to avoid background signal and to improve the reaction time to enhance capture efficiency for excellent sensitivity.

The probes used for mLFIA detection were characterized using various techniques. The morphologies of the magnetic $Fe_3O_4$/Au core-shell nanoprobes and the AuNP probes were characterized using TEM. Here, the size of the $Fe_3O_4$/Au core-shell magnetic probes 452 was between 30-50 nm, which is attributed to the quick reduction of the Au shell with $NaBH_4$, and the size of the AuNP probes 1402 was about 40 nm.

The magnetic probes 452 exhibit an absorption peak at 542 nm, corresponding to the size of the $Fe_3O_4$/Au core-shell nanostructures, while the absorption in the long wavelength region of the peak was assigned to the non-uniform shape of the obtained magnetic probes. The AuNP probes 1402 showed a typical absorption peak at 530 nm.

The peaks corresponding to Au and Fe in the EDX data of the magnetic $Fe_3O_4$/Au core-shell nanostructures (not shown) clearly evidenced the elemental construction of the $Fe_3O_4$/Au core-shell nanostructure. Zeta potential measurements were also performed (results not shown), and changes in zeta potential confirm the modification of the magnetic probes and AuNP probes 1402. Indeed, the signal was amplified with the HRP modified AuNP probes in the presence of TMB.

Figure 15:
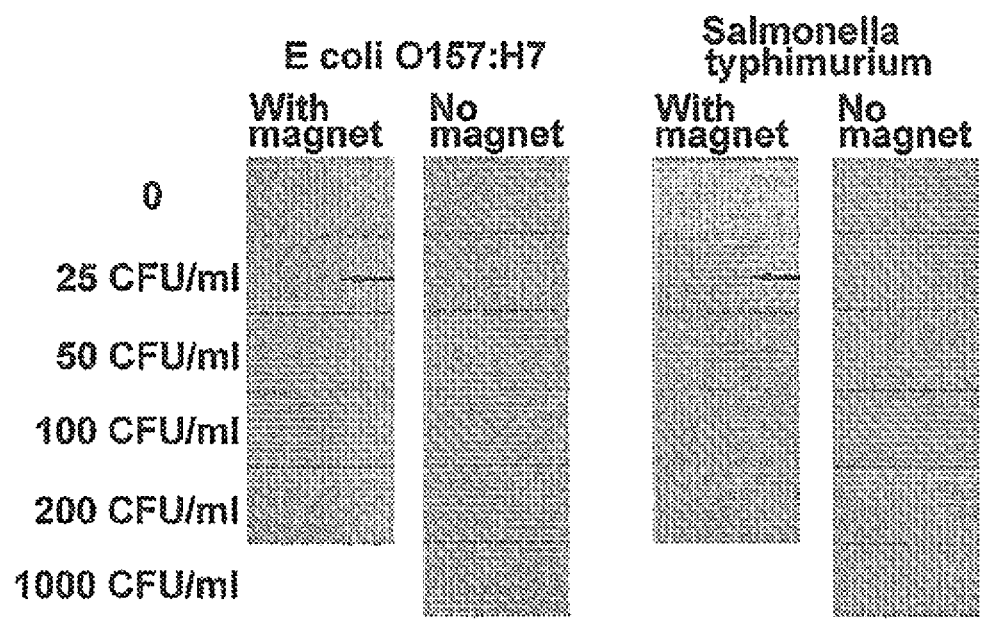
FIG. 15 shows results of the magnetic focus LFIA detection platform as compared to a control (without magnet), with arrows highlighting the obtained dots from the samples with 25 CFU per ml of pathogens.

To demonstrate the detection capability of the mLFIA for various bacteria, the probes were modified with 2 types of antibodies to detect *E. coli* O157:H7 and *Salmonella typhimurium* and the amount of magnetic probes 452 and AuNP probes 1402 was optimized for best sensitivity. Photographs of the resulting LFIA strips are shown in FIG. 15. For comparison, the results of detection without an external magnet are also shown in FIG. 15. mLFIA results show that with a magnetic field, as low as 25 CFU per ml of *E. coli* O157:H7 and *Salmonella typhimurium* can be visually observed from the dots on the strip. The volume of sample used in the mLFIA was 100 ml, indicating that as few as 2-3 cells can be detected with naked eye without the use of any readers. As the concentration of the bacteria increased from 0 to 200 CFU per ml, the color of the dot became more intense. Based on the increase in the intensity of the dots, it is possible to assess the concentration of the pathogens in the samples. For comparison, the results of detection without an external magnetic field resulted in no visual information even in the presence of bacteria at up to 1000 CFU per ml for both *E. coli* O157:H7 and *Salmonella typhimurium*.

The results with and without the external magnetic field clearly demonstrate that the external magnetic field increased detection sensitivity, which could be assigned to the increased interaction time between the labelled bacteria and antibody conjugated to the LFIA strips at the detection zone. The technique demonstrated excellent sensitivity not possible before. Indeed, with the exemplary LFIA-based approaches described herein, for the first time it is possible to detect as low as 25 CFU per ml of pathogens by visual observation. Similar results can be noted for both *E. coli* O157:H7 and *Salmonella typhimurium*, suggesting that the magnetic focus has tremendous potential in enhancing the LOD of LFIA systems, including the detection of biomarkers for cervical cancer diagnosis. The color and intensity of the signal can be used to report on the concentration of pathogens with a simple photographic analysis.

Figure 16:
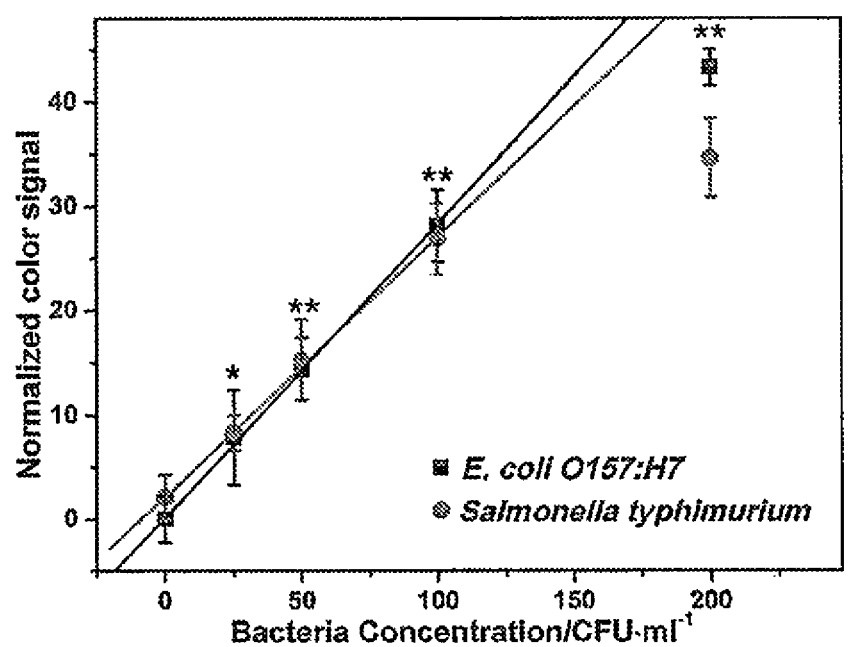
FIG. 16 shows calibration plot for the detection of *E. coli* O157:H7 (A) and *Salmonella typhimurium* (B); [Mean±SD, n=5]*$p<0.05$ vs. blank; **$p<0.01$ vs. blank.

Using appropriate software, the color of the magnetic focus enhanced dots generated from the HRP-catalyzed TMB reaction was quantified and these values were plotted as a function of the concentration of bacteria in the samples. The obtained curves are shown in FIG. 16. According to the plot obtained for the detection of *E. coli* O157:H7, it can be seen that when the concentration of *E. coli* O157:H7 is in the range between 0 and 200 CFU per ml, the normalized value of the color signal increases in proportion to the pathogen concentration. Meanwhile, an excellent linear relationship will exist between the signals and bacterial concentration in range from 0 to 100 CFU per ml. Based on the linear relationship ($R^2$=0.992), the LOD of the mLFIA for *E. coli* O157:H7 is calculated to be ~23 CFU per ml, indicating that in the proposed detection procedure 2 cells present in 100 ml of the sample can be detected. Furthermore, this LOD can be achieved within 30 min without any extra instruments, making it a very rapid, practical and a highly sensitive point-of-care on-site sensor. The results from the detection of *Salmonella typhimurium* are also recorded in FIG. 16. It can be seen that, similar to the results from *E. coli* O157:H7, as low as 25 CFU per ml of *Salmonella typhimurim* are recognized and a linear range from 0 to 100 CFU per ml is plotted ($R^2$=0.998). According to the linear relationship, a LOD for *Salmonella typhimurim* detection is calculated to be ~17 CFU per ml (~2 cells in 100 µl of sample). The obtained LODs for the detection of *E. coli* O157:H7 and *Salmonella typhimurium* are the lowest reported results using an LFIA-based approach. Pineapple juice inoculated with *E. coli* O157:H7 from 0-400 CFU per ml was also tested, with the results (not shown) confirming the applicability of the sensor in real samples.

For the magnetic focus enhanced LFIA detection platform, since the probe-labelled pathogens were slowed down at the detection zone due to the external magnet, the extended interaction time may also increase the possibility of nonspecific binding to influence the selectivity of the proposed detection strategy. During the disclosed detection method, extra washing steps with water were performed to remove the unbound probes.

Figure 17:
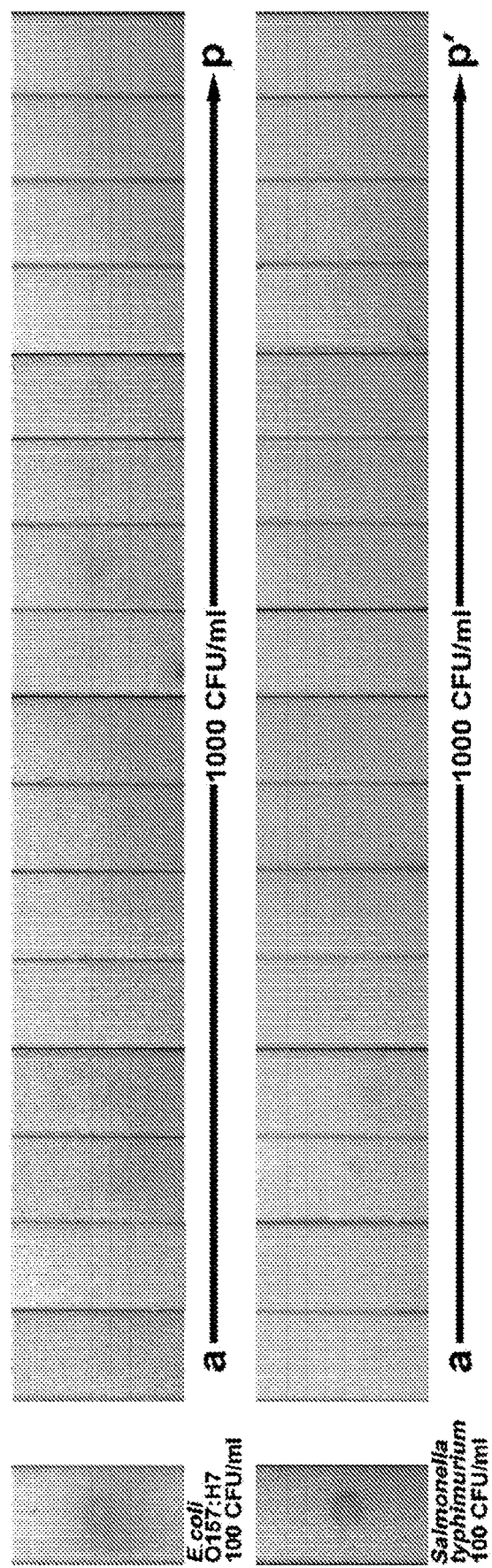
FIG. 17 shows the results of cross-reactivity experiments with 100 CFU per ml of target bacteria and 1000 CFU per ml of *E. coli* O26:H11; (a), *E. coli* O45:H2 (b), *E. coli* O145:NM (c), *E. coli* O121:H19 (d), *E. coli* O111:H8 (e), *Acinetobacter baumannii* ATCC 19606 (f), *Bacillus cereus* UW85 (g), *Hafnia alvei* (h), *E. coli* O103:H2 (i), *E. coli* O157:H7 ATCC 35150 (j), *Pseudomonas aeruginosa* (k), *Bacillus cereus* ATCC 14579 (l), *Citrobacter freundii* NRRL B-2643 (m), *Proteus mirabilis* ATCC 7002 (n), *Kurthia sibirica* (o), and *Salmonella typhimurium* (p, negative for *E. coli* O157:H7) or *E. coli* O157:H7 (p', negative for *Salmonella typhimurium*).

To demonstrate the selectivity of the magnetic focus LFIA, 16 types of pathogenic strains at 1000 CFU per ml were tested as negative controls. The results of these negative controls are shown in FIG. 17, where the concentration of the target pathogen were kept at 100 CFU per ml (for both of *E. coli* O157:H7 and *Salmonella typhimurium*). Cross-reactivity experiments supported that no perceivable signals were recognized on the strips when the concentration of the test samples (negative control) were 10-fold greater than the target. Only a weak signal was observed from the samples with 1000 CFU per ml of *E. coli* ATCC 35150 (see sample j in FIG. 17) on the LFIA strips, whereby antibodies against *E. coli* O157:H7 demonstrated some binding to *E. coli* ATCC 35150, which has the same antigenic property as the serotype *E. coli* O157:H7. The detection results from the target and 16 types of negative control pathogens clearly demonstrate the excellent selectivity of the proposed mLFIA detection method. Similar selectivity was exhibited for both *E. coli* O157:H7 and *Salmonella typhimurim* providing excellent validation of the mLFIA detection platform, suggesting excellent specificity of mLFIA in the detection of cervical cancer biomarkers.

EXAMPLE 5

Recognition of Target Proteins

To achieve the recognition of target protein VCP, anti-VCP antibody M118 was utilized to construct probes (as defined in further detail below). After blocking with casein, the obtained mNPs were then biotinylated for the conjugation of streptavidin-poly HRP, which enabled an enzyme amplified colorimetric with TMB as substrate.

To demonstrate the modification of mNPs, zeta potential of the mNPs and modified magnetic probes was recorded. As showed in Table 1, it can be seen that the modification of the mNPs increased the zeta potential from −29.7±1.6 mV to −29.7±1.6 mV.

TABLE 1

Zeta potential measurement conducted at 25° C.

| | Unmodified magnetic NPs | Magnetic probes | Magnetic probes interact with 1 µg/ml VCP |
|---|---|---|---|
| Zeta potential (mV) | −29.7 ± 1.6 | −21.2 ± 1.6 | −27.2 ± 2.1 |

In this process we utilized HRP for signal generation. As at least one alternative, platinum nanoconjugates or other color generating label reagents can be utilized.

Detection Results

Figure 18:
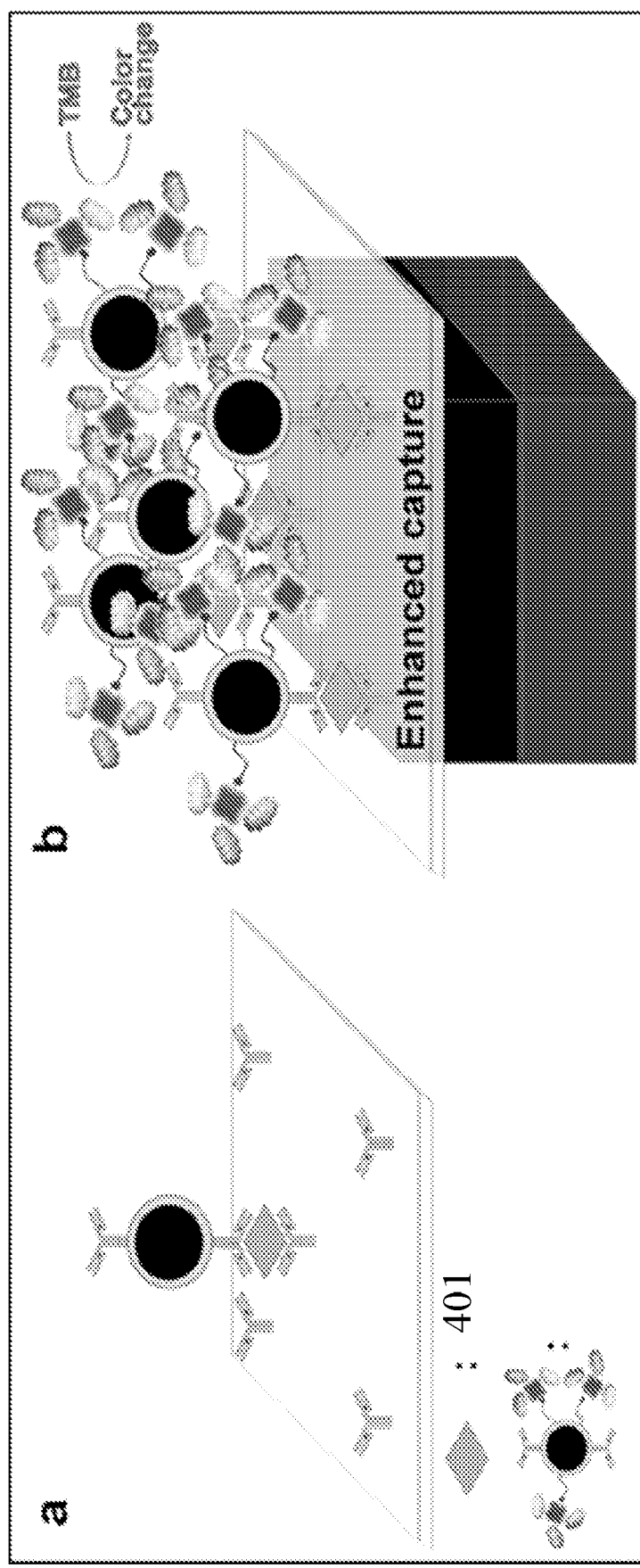
FIG. 18 illustrates the magnetic focus enhanced lateral flow VCP detection based on enzyme amplified colorimetric signal.

As shown in FIG. 18, which depicts the magnetic focus enhanced lateral flow VCP detection based on enzyme amplified colorimetric signal, the detection process does not require additional instrumentation. Indeed, the HRP amplified colorimetric signal facilitated the direct determination of the VCP target with naked eyes along with exquisite detection sensitivity. Combining the magnetic focus enhancement and HRP amplification of the novel devices, systems, and methods of the present disclosure, an extremely low concentration of VCP was detected. The detection results of VCP in PBS buffer are shown in FIG. 19.

Figure 19:
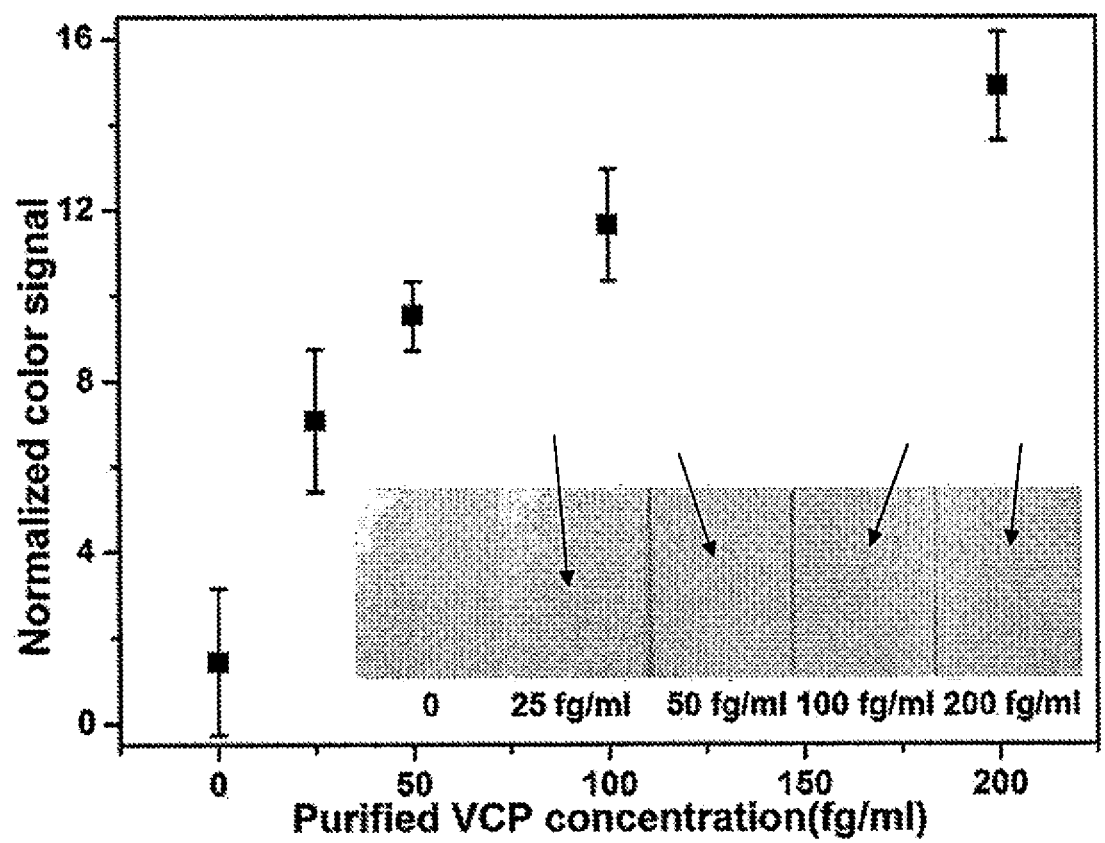
FIG. 19 show the detection results of purified VCP in PBS.

FIG. 19 clearly shows that, in the photographs of the LF strips, the color density of the dot increases according to the VCP concentrations. With 25 fg/ml VCP in PBS buffer, a dot in light blue could be recognized in the photograph (see arrow). To the best of our knowledge at the time of filing, this is the lowest detected concentration of a protein target to date. Compared with the conventional LFIA based on the colorimetric signal from GNPs or latex, the detection sensitivity dramatically improved about $10^6$ times. Compared to the efforts to enhance the LFIA with different indirect label-based LFIA, the LOD was improved more than $10^3$ times without requirement of reader, facilitating the POC application. The quantified normalized color density of the dots also showed the increased value according to the VCP concentration, supporting the accuracy of the quantitative detection capabilities of mLFIA (i.e. the mLFIA device 400) for protein targets.

To further demonstrate the detection capability of the assay devicve 400 for biological samples, a detection in tissue lysate samples was performed. After a typical tissue lysis process, the proteins were isolated with a trichloroacetic acid precipitation procedure to reduce the influence of lysis buffer to the detection. The detection performance of the mLFIA device 400 was also assessed with protein in tissue lysate diluted with PBS.

Figure 20:
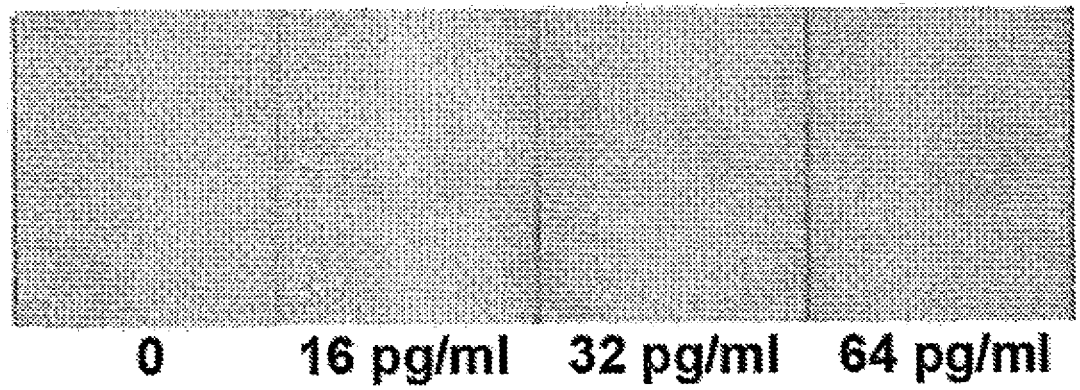
FIG. 20 shows detection results of VCP in protein mixture extracted from tissue lysate diluted with PBS in serial concentrations.

As shown in FIG. 20, in the tissue lysates with total protein as low as 16 pg/ml, VCP protein could be recognized with naked eyes. With higher concentration of total protein, the color density of the obtained dots increased, as shown in the photographs and corresponding normalized quantified blots. The capability of the mLFIA device 400 to detect a protein target in biological samples exhibited a strong potential for its applicability in the clinic.

Probe Interactions with VCP (zeta, AUC, Blot Assay, NTA)

To investigate the interaction between magnetic probes and a VCP target, various characterizations were performed. As shown in Table 1, the reduction of zeta potential of magnetic probes can be seen from −21.2±1.6 mV to −27.2±2.1 mV after the interaction with VCP. Since the isoelectric point of VCP is 5.14 (in PBS solution (pH=7.4)), the conjugation of negatively charged VCP to a magnetic probe would induce the reduction of zeta potential.

Movement of the Probe in Magnetic Field

To directly exhibit the movement of magnetic probes in the magnetic field, at first blush it seems that the optical label would be the best way. However, because the NC membrane is non-transparent and the magnetic force could drive the magnetic probe into the NC membrane and away from the surface of NC membrane, direct investigation with fluorescence label on NC membrane reveal that movement of magnetic probes in the magnetic field was challenging. Therefore, two devices were constructed to simulate the micro-channel in NC membrane for the characterization of the magnetic probes in the magnetic field like that in the mLFIA device 400 detection.

Figure 21:
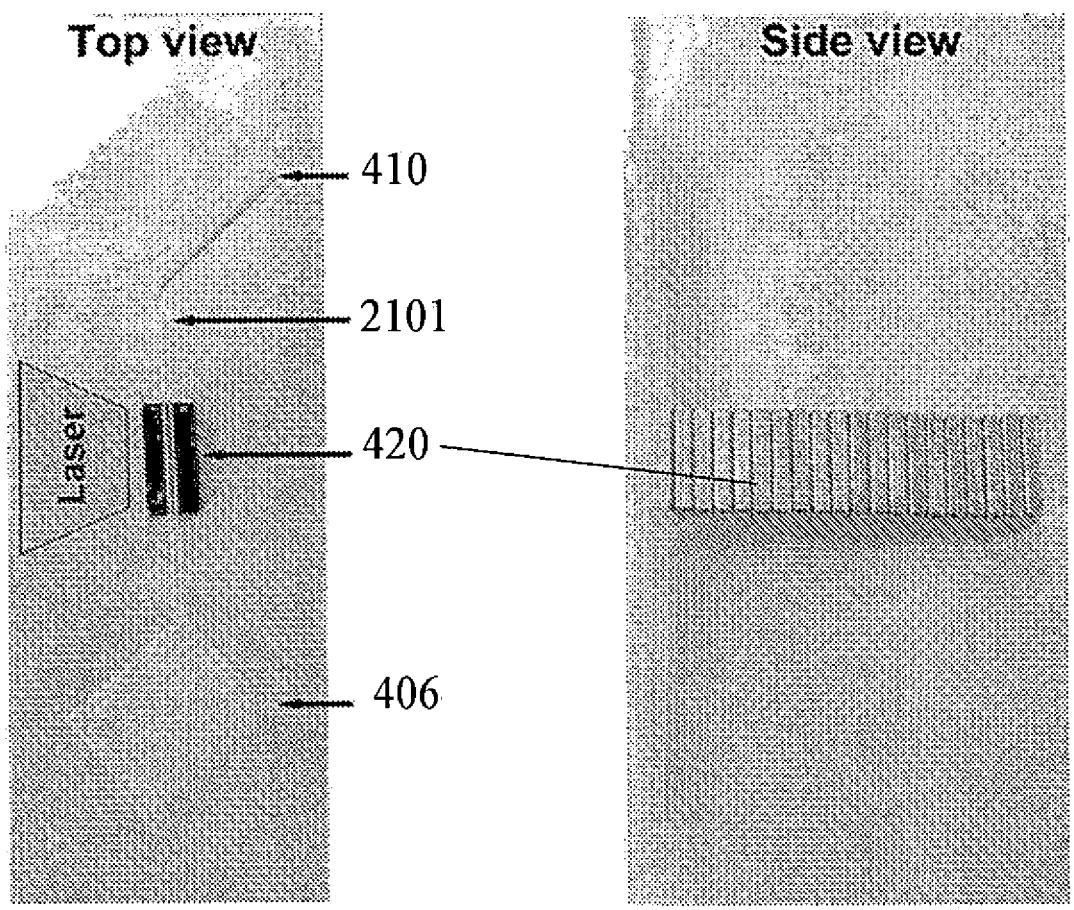
FIG. 21 shows a top view (left) and a side view (right) of a designed device for SERS characterization of magnetic nanoparticle distribution within a magnetic field, with a sample solution flowing in a capillary tube being used to simulate the flow of micro-channels in the NC membrane.

In FIG. 21, the device 400 was used to demonstrate the effect of the magnetic field generated by the magnet 420 on the movement of magnetic probes 452 in a micro-channel 2101 by surface enhanced Raman spectroscopy (SERS). The key purpose of this experiment was to show that, with a magnetic field, the movement of the target at the signal zone is reduced to allow for a high capture efficiency. The glass capillary tube 2101 was fixed on a glass slide for excitation to produce a SERS spectrum from magnetic nanoparticles 452 labelled with 4-MPy, a Raman reporter. A conjugate pad/area 406 was attached at one end of the tube 2101 to apply the sample solution, while at the other end an absorbent pad 410 was attached to drive the solution flow through the tube 2101; the corner of the pads contacts the tube 2101 for the sample flow. A magnet 420 was fixed under the middle of the capillary tube 2101 when the movement of the magnetic particles in magnetic field was tested.

During the SERS measurement, the sample solution with magnetic nanoparticles 452 modified with Raman reporter was applied on the conjugate pad/area 404, which was driven to the absorbent pad 410 through the capillary tube 2101, meanwhile a continuous SERS measurement was performed and the obtained SERS spectra were recorded according to time. Without the change in SERS activity of magnetic nanoparticles 452 due to magnetic effect, the SERS intensity could be used to reveal the number of SERS substrates magnetic nanoparticles. It is known that the magnetic nanoparticles could be concentrated under the influence of the magnetic field, to allow for an increase in SERS activity of magnetic nanoparticles due to local surface plasmon resonance due to plasmon coupling between concentrated magnetic nanoparticles. As a control, we collected the SERS spectra without the influence of the magnetic field.

FIG. 22 shows that the SERS intensity from the concentrated magnetic nanoparticles 452 due the influence of the magnetic field is much stronger than the signal from particles without the magnetic field. Thus, during the SERS measurement, the spectral intensity would be in proportional to the number of magnetic nanoparticles excited with the laser. For example, FIG. 22A shows that after 15 min of sample flow, the SERS intensity from magnetic nanoparticles sample was obviously stronger than that from the sample without the magnet, indicating that with magnetic focus, more magnetic nanoparticles are focused in the measured region.

To further characterize the difference in movement of magnetic nanoparticles with and without a magnetic field, the SERS intensity was recorded with respect to the time. The plots of normalized SERS intensity of the sample with and without magnetic field are illustrated in FIG. 22B. There the data supports that, in multiple tests, the SERS intensity from the samples was always stronger than that without the magnetic field for all measure time. This indicates that a constant higher density of magnetic nanoparticles within the magnetic field are in the process of sample flow within the capillary tube 2102. The results obtained from SERS measurement supported the hypothesis that the magnetic field has the potential to slow the movement of magnetic probes in the micro-channels in the NC membrane. Without the magnetic field, the movement of magnetic nanoparticles in the capillary tube is driven by the solution flow and the corresponding density of magnetic nanoparticles was low. With the magnetic field, the magnetic nanoparticles were not only driven by flow but the magnetic force had the potential to reduce the movement of magnetic nanoparticles, resulting in a higher density of magnetic nanoparticles in the magnetic field at the signal generation (i.e. measurement) region. Thus, a corresponding stronger SERS intensity was obtained since more magnetic nanoparticles were present at a higher density with magnetic focus.

Figure 23:
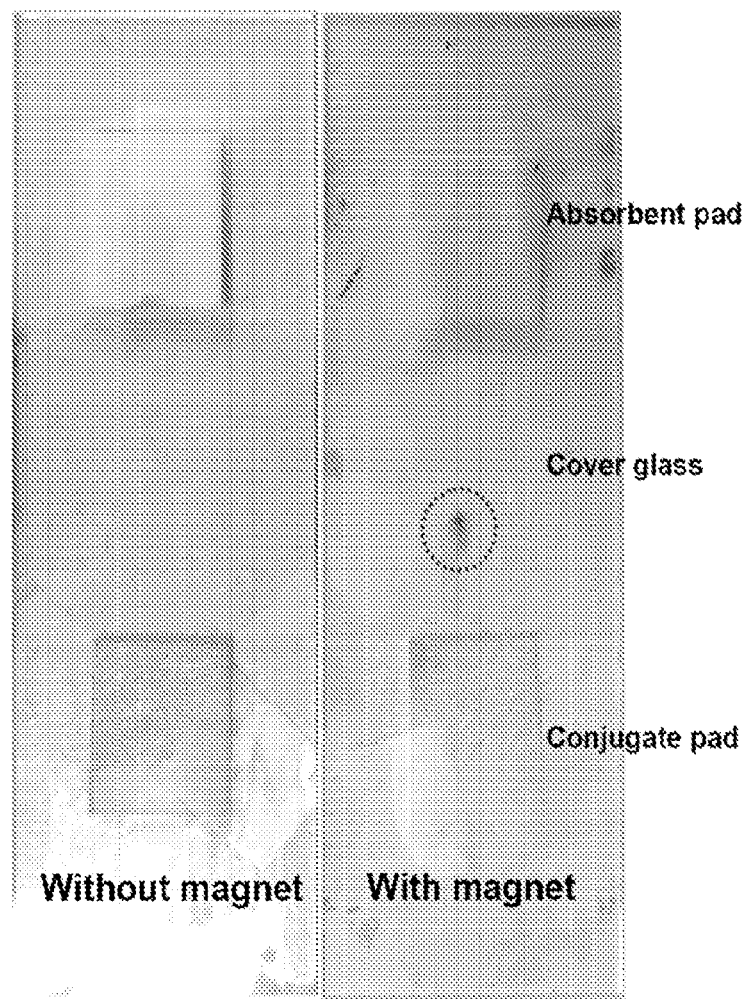
FIG. 23 shows a designed device for a dark-field image, with the ring (right) highlighting the accumulation of magnetic probes due to the magnetic field.

It can be seen in FIG. 22B that the SERS intensity from samples under the influence of a magnetic field was about 7-10 times greater than that without the magnetic field, suggesting there are 7-10 times more magnetic nanoparticles within the magnetic field. Further, a slightly increased SERS intensity with magnetic field was observed with respect to time, while the intensity without a magnetic field almost remained the same. This supports that the accumulation of magnetic nanoparticles within a magnetic field could even be directly seen with a simple photograph, as in FIG. 23. Indeed, the increased density of magnetic probes and the higher efficacy of target accumulation at the detection zone on the LF strip where the magnet was fixed as shown in FIG. 23 is one of the key reasons behind the improved detection sensitivity of the developed mLFIA (i.e. mLFIA device 400). Besides the SERS test, dark-field images were recorded to directly show the movement of magnetic probes in magnetic field (inset in FIG. 22B).

Evaluation of Probe Mobility in an mLF-IC Strip by Particle Image Velocimetry.

Particle Image Velocimetry (PIV) is a well-established technique for measuring the velocity field of flowing fluids based on imaging tracer particles carried by the fluid. Images of tracer particles taken from consecutive images may be cross-correlated to measure the particle motion from one image to the next. Here, PIV was used to analyze the effect of a magnet on particle motion as capillary flow occurs on the strip 402. An ensemble of 13 consecutive images were captured at 2 minute intervals to reduce the effects of statistical noise.

Figure 24:
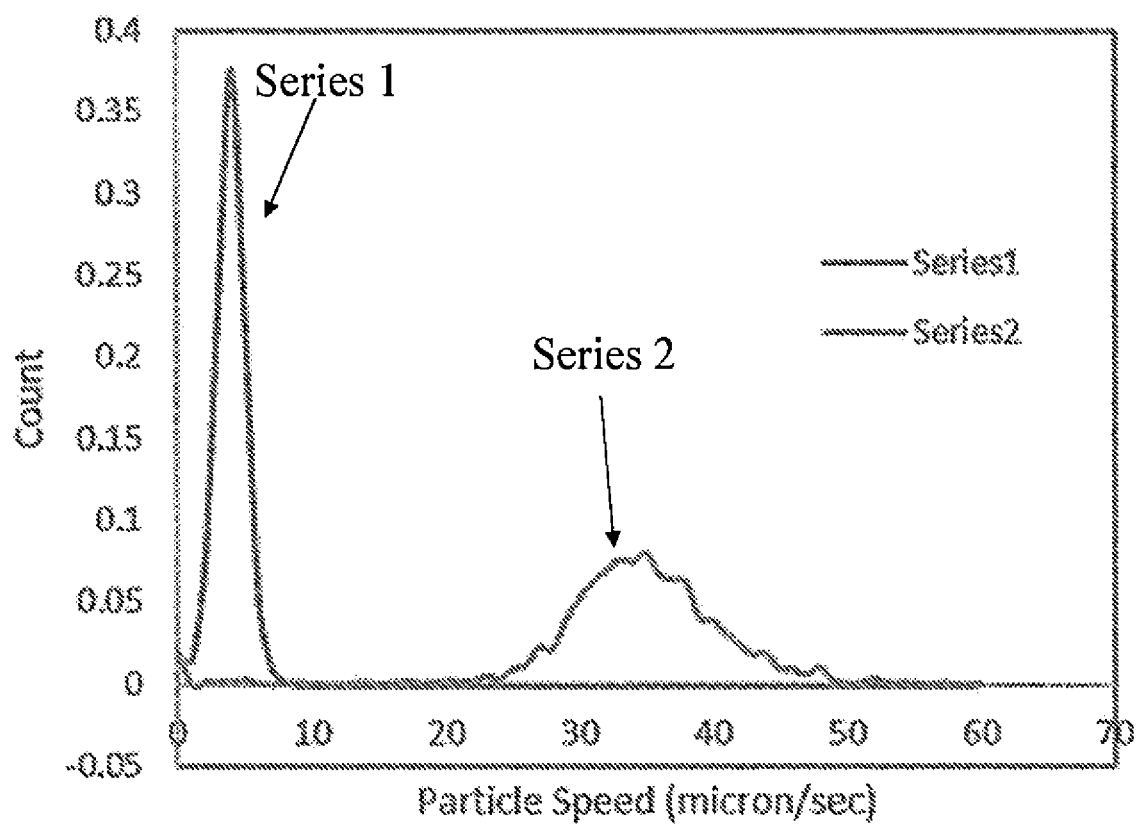
FIG. 24 shows a graph representing a velocity distribution of particles in strip of the assay device of the present disclosure, both with (Series 1) and without (Series 2) application of a magnet.

FIG. 24 shows the distribution of a fraction of the particles as a function of speed for a case when the magnet is applied (Series 1) and when the magnet is not applied (Series 2). The magnet pulls the particles to the near wall region where the speed of the flow is much slower. As noted from the Series 1 curve, the particles are drawn to the near wall region where the flow is much slower (5 micron/sec) and the range of particle speed is much smaller. When the magnet is not applied, the particles are distributed throughout the strip and show a much faster mobility (35 micron/sec), but also a broader distribution. This further validates that slower movement of the particles under the influence of the magnetic field allows for increased interaction time at the target capture zone/area 408 and, hence, an increased efficiency of target capture that results in the detection of molecules at a high level of sensitivity that heretofore has not been achieved. This data, along with the results from SERS (FIG. 22), are complementary and support that magnetically focusing the target analytes 401 in the mLFIA device 400 increases the target accumulation efficiency at the signal zone.

Notes Regarding the Preparation of the Materials for the Experiments Described Herein: Materials for Formulation of Nanoparticle Probes:

$HAuCl_4 \cdot XH_2O$, $FeCl_3$, $FeCl_2$, 4-mercaptopyridine, sodium citrate, sodium carbonate were obtained from Sigma (MO US). NaOH was purchased from Mallinckrodt Chemicals (NJ US). $NaBH_4$ was obtained from ACROS ORGANICS (NJ US). Tetramethyl benzidine (TMB) substrate solution was obtained from Moss Inc. (MD US). Pierce™ streptavidin poly-horseradish peroxidase (HRP) was obtained from ThermoFisher Scientific (NY US). All materials in the experiments were used as purchased without further purification. Glasswares used in the experiment were washed with fresh aqua regia and then rinsed with DI water multiple times.

Proteins and Antibodies.

Purified valosin-containing protein (VCP) (Catalog number: CF48) were from Novoprotein (NJ US). The anti-VCP antibodies p97/VCP Antibody (2H5) (M15) and p97/VCP Antibody (2B2) (M18) were purchased from Novus Biologicals, LLC (CO US).

Probe Preparation.

The magnetic probes were prepared based on $Fe_3O_4$-Au core-shell nanostructures. The $Fe_3O_4$ nanoparticles as magnetic core were synthesized based on the reported method with modification. Briefly, 30 mL of 0.1 M NaOH solution was heated to boiling then under strong stirring 0.2 M $FeCl_2$ and $FeCl_3$ was quickly added. After 10 min, 2 mL of 0.4 M sodium citrate solution was injected. The obtained solution was refluxed for 4 hours. The Fe3O4 synthesized was washed with ethanol and deionized ("DI") water for 3 times respectively and redispersed in 10 mL DI water. The magnetic Fe3O4-Au core-shell nanoparticles was synthesized based on a quick reduction process with NaBH4. In general, 80 μL $Fe_3O_4$ was mixed with 920 μL DI water, followed by addition of 100 μL of 1% $HAuCl_4$. The obtained mixture was sonicated for 15 min, then 200 μL of 10 mM ice-cold fresh NaBH4 was quickly injected. The resulted solution was sonicated for 15 min. The obtained $Fe_3O_4$-Au core-shell nanoparticles in dark red were washed with water for 3 times and kept at 4° C.

Gold nanoparticles ("GNPs") in around 40 nm were also used for the synthesis of probes as a comparison of the magnetic nanoparticles. To prepare GNPs, method based on Frens' work was used. 1 mL of 1% $HAuCl_4$ was added in 100 mL of DI water which was then heated to boiling. Under strong stirring, rapid addition of 1 mL of 1% sodium citrate resulted in a color change from colorless to red, indicating the formation of GNPs. The obtained GNPs was stored at 4° C.

The magnetic $Fe_3O_4$-Au core-shell nanoparticles and GNPs were functionalized with biotin and antibody to recognize the target protein VCP in same procedure based on our previous report. 1 mL of nanoparticles was well mixed with 1 μL of 0.5 M Sodium carbonate and 100 μL of 10 mM phosphate buffer (pH=7.4). Then 10 μg M18 antibody was added to the solution which was then shaken for 2 hours. To block the residual surface of nanoparticles, 122 μL of 5% casein in 10 mM phosphate buffer was added for overnight blocking under gentle shaking. With centrifugation, unbound antibody was removed and the obtained nanoparticles were redispersed in 1 mL of 10 mM phosphate buffer. To biotinylate the nanoparticles modified with antibody, 10 μg of sulfo-NHS-LC-biotin was added for 1 hour reaction under gentle shaking, followed by the addition of 0.1 mL of 5% casein in 10 mM phosphate buffer. After 1 hour, the obtained modified nanoparticles were washed and redispersed in 100 μL of 5% casein in 10 mM PBS, which were then kept at 4° C. for the target protein detection.

Lateral Flow Strip Assembly.

The lateral flow strips used in the experiments were assembled on plastic backing cards (mdi Membrane Technologies, PA, US) in size of 6.0 cm×0.5 cm composite of four parts: nitrocellulose membrane (90CNPH-N-SS40 from mdi Membrane Technologies, PA, US) 2.5 cm×0.5 cm, absorbent pad (Grade 17 Chr Cellulose Chromatography Papers from GE Healthcare Life Sciences, MA, US) 1.5 cm×0.5 cm, conjugate pad (Grade 6613H from Ahlstrom North America, GA, US) 1.1 cm×0.5 cm, and sample pad (Sample Pad Type GFB-R4 from mdi Membrane Technologies, PA, US) 1.7 cm×0.5 cm. The nitrocellulose membrane was first attached on the plastic backing card at the position 1.3 cm from one end where absorbent pad was attached. From the other side of nitrocellulose membrane, conjugate pad and sample pad were attached. There is 0.2 cm overlap between each part.

Samples to be Utilized in the Strip Assay.

Proteins and pathogens suspended in PBS buffer, saliva, urine, and blood with minimal to no sample preparation.

Biomarker Detection.

To conjugate the antibody (M15) to the LF strips, 0.33 μg M15 antibody (PBS solution) was transferred on each LF strip which was then dried at 37° C. for 1 hour. The obtained LF strip were placed in a 3D printing-prepared device where an external magnet (N52 rare earth neodymium permanent super strong magnet) was fixed under the strip.

The as-prepared probes were mixed with 100 μL of liquid sample as well as 10 μg/ml streptavidin poly-HRP. The obtained mixture was kept stable for 10 min for the capture of the probes to VCP target. Then it is loaded on the samples pad of the LF strip for a 15 min sample flow. The LF strip was washed with 60 μL DI water twice with additive conjugate pad and absorbent pad in the cross direction every 5 min. Thirty μL of TMB substrate was applied twice for the generation of colorimetric signal with incubation at room temperature for 5 min. Then the LF strip was washed with 60 μL DI water. Photograph was taken to record the final results and the analysis was performed with software of ImageJ (National Institutes of Health, US). After the normalization of the photographs, the quantified results were obtained from the gray scale of the part with deepest color at the dot subtracting the average gray scale of the blank part of the strip.

Characterization.

UV-vis spectra of the nanoparticles and probes were recorded with a Jasco V570 UV/Visible/NIR spectrophotometer (Jasco, Inc.). Zeta potential measurement was conducted with a Zetasizer NanoZS (Malvern Instruments). The TEM images of the samples were collected with a FEI Tecnai G2 20 with the operation at 100 kV. Raman measurement was performed with a SENTERRA confocal Raman system (Bruker Optics) with 20×long WD objective and 785 nm excitation. To collect the dark-field images, a home-built hyperspectral dark-field imaging (HSDFI) system from our previous work was utilized.

In conclusion, the inventive systems and methods of the present disclosure provide a simple, rapid and practical, yet ultrasensitive, analytic strategy for naked eye detection of pathogens enhanced by mLFIA. Using magnetic probes and an external magnet placed below the strip, the interaction time between the labelled target pathogens and capture antibody is increased, resulting in a significant signal enhancement for visual detection at a LOD as low ~23 CFU per ml for *E. coli* O157:H7 and ~17 CFU per ml for *Salmonella typhimurim* which are the best results reported for whole bacteria detection by naked eye colorimetry without any pre-enrichment. Since the detection was performed with 100 ml of sample volume, the LOD achieved implies that 2-3 cells per strip can be detected, nearing the limit of LFIA-based detection of whole bacterium. The results from *E. coli* O157:H7 and *Salmonella typhimurim* demonstrate that the disclosed strategy can be extended to detect a range of other pathogens or biomarkers with an unprecedented LOD. The magnetic focus enhanced LFIA concept is highly significant and could be deployed as an on-site point-of-care screening tool to detect pathogens and other disease biomarker including the biomarkers of cervical cancer. The excellent detection performance of mLFIA, both in sensitivity and specificity, demonstrates a highly promising analytical tool for the detection of selected biomarkers for cervical cancer diagnosis in a simple, rapid, practical and economical manner.

Accordingly, unlike conventional techniques, the devices, systems, and methods of the present disclosure are affordable, accurate, and easy-to-use for POC diagnosis of cervical cancer. Furthermore, some of the technical advantages of the Cross-Path platform compared to conventional Lateral flow are as follows:

1. Significantly Increases Analytical and Clinical Sensitivity.
    a) The mLFIA device 400 and related method 460 show substantially improved sensitivity, from 30-100×more sensitive than the existing commercial Lateral Flow (II) IC units.
    b) Free migration paths for the sample and conjugate account for this increased sensitivity coupled with more effective binding of the analyte to the capture ligands in the test zone prior to the enzyme catalyzed reaction of the conjugated marker complex at the test zone. With one cross flow of TMB (FIG. 7A) the strips bearing the four proteins can be simultaneously highlighted.
    c) The use of aptamers provides an opportunity to work with capture ligands that are more pH and temperature stable compared to antibodies, yielding a better shelf life. Aptamers are small single-stranded nucleic acids that have the ability to fold into well-defined 3-dimensional structures with potential for high affinity and specificity to their target molecules. Further aptamers are easy to produce once the sequences are optimized (which is one of our goals in this effort) and have the potential to be more specific. Aptamers are much smaller in size compared to antibodies and higher numbers can be attached to the enhancing substrates to increase capture efficiency.
2. Decreased Overall Assay Interaction Time
    a) Samples such as blood, saliva and cells are known to migrate very slowly in conventional LF assays, but with separate and independent migration paths sorbent material may be utilized to permit faster migration without the concern for the conjugate migration requirements.
    b) Speed of the disclosed platform assays are similar to the existing units, and exhibit increased sensitivity, due to improved background clearance from better uniformity and consistency of migration of the conjugate particles in the absence of the sample particles.
3. Cross Path Platform is able to effectively resolve normal aggregation/agglutination migratory issues, a common concern in LF assays with large particle analytes: this approach allows assays to be extremely sensitive and specific with an LOD at least $10^2$-$10^3$-fold better than the existing LF units with a potential to further enhance the signal to achieve 400-fold enhancement.
4. Enhanced multiplex capability with independent and simultaneous delivery of samples: cross path platform using our cross lateral flow-IC (CLFIA) approach provides multiple analyte results with a high degree of sensitivity without compromising specificity.
    a) Analytes are able to migrate freely without the conjugate and reach the test zone independently and are thus able to bind equally so that the same level of sensitivity is maintained across all different analytes.
    b) Enhanced calorimetric detection is almost simultaneous since the enzyme reacting reagent will flow in the horizontal direction (FIG. 7A) while the sample flows in the vertical direction.
    c) Easier to read results due to the fact that different colored latex particles can be used to conjugate different aptamers or antibodies provided in the conjugated pad or in the buffer solution.
5. Easier and user-friendlier test procedure: the technology described herein as compared to the available LF devices is almost as rapid because the cross flow path of the enzyme reacting reagent is almost simultaneous and the analysis can be completed in 15-30 minutes, if not sooner. The device is as user-friendly as the existing systems, because the user only needs to apply the sample with other existing LF systems. Quantification is also not complex, because it only requires a photograph be taken by the user to have the results evaluated and displayed in a hand-held device. Alternatively, if a reader is used, the user need only slide the immune strip in the reader and initiate the camera and the results will be displayed after a simple image analysis.

In sum, exemplary embodiments of the present disclosure are intended as a single use point-of-care test to aid in the diagnosis of high-grade intraepithelial cervical lesions as well as for use in connection with screening for food pathogens or other pathogenic infections. Certain embodiments of the test tool described herein will have one or more of the following characteristics:

It is simple, flexible, safe, affordable and portable

The test will provide sharp and distinctive visual colorimetric bands that can be easily interpreted by a mid-level trainee It is convenient and cost effective and thus ideally suited for field-testing. All tests can be performed in ambient temperature, all reagents will have a long shelf life tested for specificity, and no special laboratory equipment will be required. We will utilize the knowhow of our industry partner and their experience in shelf life testing and storability assessments, based on their current market success in the products they have in place.

Time as well as labor saving; kits are provide that contain Ready-to-Use Reagents and are useful with only a simple procedure, total test time of 15 to 30 minutes providing high sensitivity (>100-fold with a potential to increase up to 400-fold compared to available tests) and specificity [analogous to HIV tests used in the same environments]

The ability to quantify the reaction with a simple cell phone camera built-in with calibration standards for on-site detection While various embodiments of compositions, systems, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or too limiting. The scope of the disclosure is to he defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. An assay device for detecting the presence or absence of one or more target analytes in a fluid sample, the assay device comprising:
    one or more strips of a porous substrate comprising:
        a first conjugate area comprising one or more conjugates, each conjugate for binding a target analyte if present within a fluid sample to form a target analyte complex, wherein (a) at least one of the one or more conjugates comprises magnetic probes for labeling a target analyte if present (b) the fluid sample comprises magnetic probes for labeling a target analyte if present or both (a) and (b), such that the target analyte complex, if present, is labeled with one or more magnetic probes, and
        a capture area in flow contact with the first conjugate area and comprising one or more immobilized capture ligands coupled thereto, each of the one or more immobilized capture ligands comprising an antibody or an aptamer specific to the target analyte; and
    at least one magnet positioned at or near the capture area of the one or more strips, the at least one magnet configured to magnetically interact with the target analyte complex labeled with one or more magnetic probes to reduce a flow rate of the magnetic probe labeled target analyte complex through the capture area;
    wherein the first conjugate area and the capture area each support flow of the fluid sample along a first flow direction and generation of a signal in the capture area is indicative of a target analyte being present within the fluid sample.

2. The assay device of claim 1, further comprising at least one supply area comprising a porous substrate positioned laterally of the capture area, the at least one supply area supporting flow of an agent received thereon to the capture area along a second flow direction, the agent for generating a signal upon contact with a target analyte complex.

3. The assay device of claim 2, wherein the at least one supply area further comprises an agent comprising an enzymatic substrate for generating a signal when in contact with a target analyte complex bound to the one or more immobilized capture ligands of the capture area.

4. The assay device of claim 3, wherein the enzymatic substrate comprises tetramethyl benzidine and is formulated to generate a colorimetric signal upon reaction with the conjugate of the target analyte complex.

5. The assay device of claim 1, wherein the at least one magnet is further configured to exert a magnetic field on the magnetic probe labeled target analyte complex to focus flow of the magnetic probe labeled target analyte complex to a specified position in the capture area.

6. The assay device of claim 5, wherein the specified position comprises a concentration of capture ligands.

7. The assay device of claim 1, wherein the one or more conjugates comprises an enzyme-catalyzed tracer.

8. The assay device of claim 1, wherein the enzyme-catalyzed tracer further comprises a streptavidin construct having at least one horseradish peroxidase molecule chemically coupled thereto to generate a colorimetric signal upon reaction with the conjugate of the target analyte complex.

9. The assay device of claim 1, wherein the target analyte comprises a protein, a microorganism, or a molecule smaller than a microorganism comprising a polysaccharide molecule or a peptide.

10. The assay device of claim 1, wherein the target analyte comprises a molecule smaller than a microorganism.

11. The assay device of claim 1, wherein:
at least one of the one or more immobilized capture ligands comprises an antibody or an aptamer specific to a first target analyte that, upon binding a first target analyte complex formed between the conjugate and the first target analyte, immobilizes the first target analyte complex at a first attachment site;
the conjugate of the first target analyte complex generates a first signal at the first attachment site upon contact with an enzymatic substrate;
at least one of the one or more immobilized capture ligands comprises an antibody or an aptamer specific to a second target analyte that, upon binding a second complex formed between the conjugate and the second target analyte, immobilizes the second target analyte complex at a second attachment site;
the conjugate of the second target analyte complex generates a second signal at the second attachment site upon contact with an enzymatic substrate; and
visibility of the first signal is indicative of the first target analyte being present within the fluid sample and visibility of the second signal is indicative of second target analyte being present within the fluid sample.

12. The assay device of claim 11, wherein:
at least one of the one or more immobilized capture ligands comprises an antibody or an aptamer specific to the third target analyte that, upon binding a third target analyte complex formed between the conjugate and the third target analyte, immobilizes the third target analyte complex at a third attachment site;
the conjugate of the third target analyte complex generates a third signal at the third attachment site upon contact with an enzymatic substrate;
at least one of the one or more immobilized capture ligands comprises an antibody or an aptamer specific to a fourth target analyte that, upon binding a fourth complex formed between the conjugate and the fourth target analyte, immobilizes the fourth target analyte complex at a fourth attachment site upon contact with an enzymatic substrate;
the conjugate of the fourth target analyte complex generates a fourth signal at the fourth attachment; and
visibility of the third signal is indicative of the third target analyte being present within the fluid sample and visibility of the fourth signal is indicative of the fourth target analyte being present within the fluid sample.

13. The assay device of claim 1, wherein the fluid sample comprises saliva, urine, blood, or cells suspended in a buffer solution.

14. The assay device of claim 1, comprising a limit of detection of less than 100 pg/ml of the fluid sample.

15. The assay device of claim 1, wherein the first conjugate area, and the capture area each comprise a separate pad attached to a first side of an impermeable or hydrophobic barrier, with the receiving area and the first conjugate area positioned to overlap each other and the first conjugate area and the capture area positioned to overlap each other.

16. The assay device of claim 15, wherein the at least one magnet is affixed to a second side of the impermeable or hydrophobic barrier.

17. The assay device of claim 1, wherein the porous substrate comprises a capillary flow matrix.

18. The assay device of claim 1, wherein the magnetic probes comprise gold-based magnetic nanoparticles.

* * * * *